United States Patent [19]
Jang

[11] Patent Number: 6,123,721
[45] Date of Patent: *Sep. 26, 2000

[54] TUBULAR STENT CONSISTS OF CHEVRON-SHAPE EXPANSION STRUTS AND IPSILATERALLY ATTACHED M-FRAME CONNECTORS

[76] Inventor: G. David Jang, 30725 Eastburn La., Redlands, Calif. 92374

[*] Notice: This patent issued on a continued prosecution application filed under 37 CFR 1.53(d), and is subject to the twenty year patent term provisions of 35 U.S.C. 154(a)(2).

[21] Appl. No.: 09/251,650
[22] Filed: Feb. 17, 1999

Related U.S. Application Data

[60] Provisional application No. 60/074,840, Feb. 17, 1998.
[51] Int. Cl.⁷ ............................................. A61F 2/06
[52] U.S. Cl. ....................................................... 623/1
[58] Field of Search ................... 623/1, 11, 12; 606/191, 192, 194, 195, 198, 108

[56] References Cited

U.S. PATENT DOCUMENTS

| | | |
|---|---|---|
| 5,449,373 | 9/1995 | Pinchasik et al. . |
| 5,697,971 | 12/1997 | Fischell et al. ............................. 623/1 |
| 5,776,161 | 7/1998 | Globerman . |
| 5,810,872 | 9/1998 | Kanesaka et al. ..................... 606/198 |
| 5,922,021 | 7/1999 | Jang . |
| 5,948,016 | 9/1999 | Jang ......................................... 623/1 |

FOREIGN PATENT DOCUMENTS

| | | |
|---|---|---|
| 0 679 372 A2 | 11/1995 | European Pat. Off. . |
| 296 08 037 U 1 | 8/1996 | Germany . |
| 297 02 671 U 1 | 5/1997 | Germany . |
| 97/32543 | 9/1997 | WIPO ............................... A31F 2/06 |
| 97/40780 | 11/1997 | WIPO ............................... A61F 2/06 |
| WO 97/40781 | 11/1997 | WIPO . |

*Primary Examiner*—Michael Buiz
*Assistant Examiner*—Vy Q. Bui
*Attorney, Agent, or Firm*—Wilson Sonsini Goodrich & Rosati

[57] ABSTRACT

A stent in a non-expanded state has a first column expansion strut pair that includes a first expansion strut, a second expansion strut and a joining strut. A plurality of the first column expansion strut pair form a chevron shaped slot in a first expansion column. A second column expansion strut pair has a first expansion strut, a second expansion strut and a joining strut. A plurality of the second column expansion strut pair form a chevron shaped slot in a second expansion column. A plurality of first serial connecting struts form a first serial connecting strut column. The plurality of first serial connecting struts couple the first expansion column to the second expansion column. The first serial connecting strut ipsilaterally couples the second expansion strut of the first expansion column to the second expansion strut of the second expansion column.

52 Claims, 6 Drawing Sheets

TUBULAR STENT CONSISTS OF CHEVRON-SHAPE EXPANSION STRUTS AND IPSILATERALLY ATTACHED M-FRAME CONNECTORS

This application claims benefit of Provisional Application 60/074,840 filed Feb. 17, 1998.

FIELD OF THE INVENTION

This invention relates to intravascular stents, and more particularly to an intravascular stent which provides easy introduction through tortuous vessels and has a full vessel wall coverage.

DESCRIPTION OF THE RELATED ART

Angioplasty, either coronary or general vascular has advanced to become the most effective means for revascularization of stenosed vessels. In the early 1980's, angioplasty first became available for clinical practice in the coronary artery, and has since proven an effective alternative to conventional bypass graft surgery. Balloon catheter dependent angioplasty has consistently proven to be the most reliable and practical interventional procedure. Other ancillary technologies such as laser based treatment, or directional or rotational atherectomy, have proven to be either of limited effectiveness or dependent on balloon angioplasty for completion of the intended procedure. Restenosis following balloon-based angioplasty is the most serious drawback and is especially prevalent in the coronary artery system.

Many regimens have been designed to combat restenosis, with limited success, including laser based treatment and directional or rotational atherectomy. Intravascular stenting, however, noticeably reduces the restenosis rate following angioplasty procedures. The procedure for intravascular stent placement typically involves pre-dilation of the target vessel using balloon angioplasty, followed by deployment of the stent and expansion of the stent such that the dilated vessel walls are supported from the inside.

The intravascular stent functions as scaffolding for the lumen of a vessel. The scaffolding of the vessel walls by the stent serve to: (a) prevent elastic recoil of the dilated vessel wall, (b) eliminate residual stenosis of the vessel; a common occurrence in balloon angioplasty procedures, (c) maintain the diameter of the stented vessel segment slightly larger than the native unobstructed vessel segments proximal and distal the stented segment and (d) as indicated by the latest clinical data, lower the restenosis rate. Following an angioplasty procedure, the restenosis rate of stented vessels has proven significantly lower than for not stented or otherwise treated vessels; treatments include drug therapy and other methods mentioned previously.

Another benefit of vessel stenting is the potential reduction of emergency bypass surgery arising from angioplasty procedures. Stenting has proven to be effective in some cases for treating impending closure of a vessel during angioplasty. Stenting can also control and stabilize an unstable local intimal tear of a vessel caused by normal conduct during an angioplasty procedure. In some cases, an incomplete or less than optimal dilatation of a vessel lesion with balloon angioplasty can successfully be opened up with a stent implant.

Early in its development, the practice of stenting, especially in coronary arteries, had serious anticoagulation problems. However, anticoagulation techniques have since been developed and are becoming simpler and more effective. Better and easier to use regimens are continuously being introduced, including simple outpatient anticoagulation treatments, resulting in reduced hospital stays for stent patients.

An example of a conventional stent patent is U.S. Pat. No. 5,102,417 (hereafter the Palmaz Patent). The stent described in the Palmaz Patent consists of a series of elongated tubular members having a plurality of slots disposed substantially parallel to the longitudinal axis of the tubular members. The tubular members are connected by at least one flexible connector member.

The unexpanded tubular members of the Palmaz Patent are overly rigid so that practical application is limited to short lengths. Even with implementation of the Multi-link design with flexible connector members connecting a series of tubular members, longer stents can not navigate tortuous blood vessels. Furthermore, the rigidity of the unexpanded stent increases the risk of damaging vessels during insertion. Foreshortening of the stent during insertion complicates accurate placement of the stent and reduces the area that can be covered by the expanded stent. There is, further, no method of programming the stent diameter along its longitudinal axis to achieve a tapered expanded stent, and no method of re-enforcement of stent ends or other regions is provided for.

Another example of a conventional stent patent is WO 96/03092, the Brun patent. The stent described in the Brun patent is formed of a tube having a patterned shape, which has first and second meander patterns. The even and odd first meander patterns are 180 degrees out of phase, with the odd patterns occurring between every two even patterns. The second meander patterns run perpendicular to the first meander patterns, along the axis of the tube.

Adjacent first meander patterns are connected by second meander patterns to form a generally uniform distributed pattern. The symmetrical arrangement with first and second meander patterns having sharp right angled loops that allows poor surface modulation, causing to catch or snag on the irregular atheromatous vessel wall during delivery with potential damage to the vessel wall. Furthermore, the large convolutions in the second meander pattern are not fully straightened out during expansion causing potential damage to the expansion balloon if a jailbreak opening of the cell is attempted. These and other conventional stent designs suffer in varying degrees from a variety of drawbacks including: (a) inability to negotiate bends in vessels due to columnar rigidity of the unexpanded stent; (b) lack of axio-lateral structural strength of the expanded stent; (c) significant foreshortening of the stent during expansion; (d) limited stent length; (e) high metal fraction in an expanded state; (f) poor crimping characteristics; and (g) rough surface modulation of both the unexpanded and expanded state of the stent; (h) tuliping of the stent struts; (I) poor jail-break quality, etc.

There is a need for a stent with sufficient longitudinal flexibility in the unexpanded state to allow for navigation through tortuous vessels. There is a further need for a stent that is structurally strong in the unexpanded state such that risk of damage or distortion during delivery is minimal. A further need exists for a stent that maintains substantially the same longitudinal length during expansion to allow greater coverage at the target site and simplify proper placement of the stent. Yet a further need exists for a stent design with sufficient longitudinal flexibility that long stents of up to 100 mm can be safely delivered through tortuous vessels. There is a need for a stent that is configured to expand to variable diameters along its length, such that a taper can be achieved in the expanded stent to match the natural taper of the target vessel. A need exists for a stent which, (i) can be crimped tightly on the expansion balloon while maintaining a low profile and flexibility, (ii) has a smooth surface modulation when crimped over a delivery balloon, to prevent catching and snagging of the stent on the vessel wall during delivery or (iii) with reenforcement rings on the ends or middle or both to keep the ends of the stent securely positioned against the vessel walls of the target blood vessel.

SUMMARY OF THE INVENTION

Accordingly an object of the present invention is to provide a full vessel wall scaffolding of an interior lumen of a vessel.

Another object of the invention is to provide a stent, which prevents recoil of the vessel following angioplasty.

A further object of the invention is to provide a stent that maintains a larger vessel lumen compared to the results obtained only with balloon angioplasty.

Yet another object of the invention is to provide a stent that reduces foreshortening of a stent length when expanded.

Another object of the invention is to provide a stent with increased flexibility when delivered to a selected site in a vessel.

A further object of the invention is to provide a stent with a low profile when crimped over a delivery balloon of a stent assembly.

Yet a further object of the invention is to provide a stent with reduced tuliping of a stent frame.

Another object of the invention is to provide a stent that reduces vessel "hang up" in a tortuous vessel or a vessel with curvature.

A further object of the invention is to provide a chain mesh stent that increases radial and axio-lateral strength of the expanded stent.

These and other objectives of the invention are achieved in a stent in a non-expanded state. The stent of present invention is a 3-dimensional object with a generally tubular geometry, which includes inner and outer surface, inner and outer diameters, an internal tubular lumen, the wall thickness and a prescribed length. To describe the design geometry of the stent of present invention, cut-open 2-dimensional illustrations are used extensively in this provisional application. Although description of the stent strut configuration is according to the 2-dimensional cut-open drawings, the real stent of present invention is a 3-dimensional tubular object designed to function as a vessel wall scaffolding device inside a blood vessel or an anatomic tubular structure of any kind in which the stent can be implanted.

A first expansion column includes of a plurality of first expansion strut pairs of chevron-shape in upright position with the vertex or apex of chevron pointing upward. A first expansion strut pair includes a first expansion strut of generally a chevron-shape, which has a stepped-apex configuration at the center and is dissimilar to a second expansion strut configuration, adjacent to a second expansion strut of generally a chevron-shape with a simple apex. A first joining strut couples the first and second expansion struts of chevron-shape at a proximal end of a first expansion strut pair to form a closed loop. When a first expansion strut pair is joined by a first joining strut to form a closed loop, a chevron-shaped slot is formed inside the first expansion strut pair, with a narrower slot width in the closed loop half and a wider slot width in the open half due to the dissimilar chevron-shapes of the first and second first expansion struts of a first expansion strut pair. A second expansion strut pair includes a third expansion strut of chevron-shape, which has a stepped-apex configuration at the center and is dissimilar to a second expansion strut configuration, adjacent to a second expansion strut of chevron-shape with a simple-apex. A second joining strut couples the second and third expansion struts at a distal end of the second expansion strut pair to form a closed loop. When a second expansion strut pair is joined by a second joining strut to form a closed loop, a chevron-shaped slot is formed inside the second expansion strut pair, with a narrower slot width in the closed-loop half and a wider slot width in the open half, due to the dissimilar chevron-shapes of the second and third expansion struts of a second expansion strut pair. A third expansion strut pair includes a fourth expansion strut of chevron-shape with a simple-apex adjacent to the third expansion strut of chevron-shape, which has a stepped-apex configuration at the center and is dissimilar to a third expansion strut configuration. A third joining strut couples the third and fourth expansion struts at a proximal end of the third expansion strut pair to form a closed loop. When a third expansion strut pair is joined by a third joining strut to form a closed loop, a chevron-shaped slot is formed inside the third expansion strut pair, with a narrower slot width in the closed-loop half and a wider slot width in the open half, due to the dissimilar chevron-shapes of the third and fourth expansion struts of a third expansion strut pair. A fourth expansion strut pair includes a fifth expansion strut of chevron-shape, which has a stepped-apex configuration at the center and is dissimilar to a fourth expansion strut configuration, adjacent to a fourth expansion strut of chevron-shape with a simple-apex. A fourth joining strut couples the fourth and fifth expansion struts at a distal end of the fourth expansion strut pair. When a fourth expansion strut pair is joined by a fourth joining strut to form a closed loop, a chevron-shaped slot is formed inside the fourth expansion strut pair, with a narrower slot width in the closed-loop half and a wider slot width in the open half, due to the dissimilar chevron-shapes of the fourth and fifth expansion struts of a fourth expansion strut pair. These expansion strut pairs of two dissimilar chevron-shape coupled by a joining struts to form a closed loop in an alternating proximal or distal end of the expansion strut pairs can be repeated to make the prescribed number of continues chain of expansion strut pairs around the circumference in an unbroken fashion in the stent of present invention. A set of two consecutive chevron-shaped expansion strut pairs in an unbroken sequence is called expansion strut cycles. In this application, the illustrations contain six (6) chevron-shaped expansion strut pair cycles or twelve (12) chevron-shaped expansion strut pairs in a first expansion column in the 2-dimensional cut-open drawings. However, the number of chevron-shaped expansion strut pair or expansion strut pair cycle in a first expansion column can variably be changed according to the application requirements of the specific stent made of present invention. The variation of the number of expansion strut pair or expansion pair cycle in a first expansion column is within the scope of a tubular stent of present invention.

Although the illustrations in this application shows only a neutrally arranged up-right expansion strut pairs of chevron-configuration within the first, second or third expansion strut columns; the expansion strut pairs of chevron-configuration can be arranged in any tilted angulation within their assigned expansion columns. The first and second expansion struts of chevron-shape in a first expansion strut pair are parallel to each other, but the first and second expansion struts of chevron-shape in a first expansion strut pair do not parallel to the longitudinal axis of the tubular stent. The proximal or distal half of a first expansion strut pair in the first expansion column can be arranged to parallel to the longitudinal axis of the stent. Such an arrangement would also change the axis of the connecting tem of the connector strut between the two companion expansion columns. However, the first and second expansion struts of chevron-shape in a first expansion strut pair do not have to parallel to each other, either. Both the parallel and non-parallel arrangement of the first and second expansion struts of chevron-shape in a first expansion strut pair in relation to the longitudinal axis of the stent are within the scope of this invention. The first and second expansion struts of chevron-shape in a first expansion strut pair in a first expansion column can be made of two dissimilar chevron patterns as shown in the illustrations of this provisional application. However, the first and second expansion struts of chevron-shape in a first expansion strut pair in a first expansion column can be made of similar chevron-shapes; the first and second expansion struts in a first expansion strut pair may consists of two chevron-shape struts of simple-apex or the first and second expansion struts in a first expansion strut pair may consists of two chevron-shape struts of stepped-apex. Any other variations of basic chevron configuration of similar or dissimilar combination in a first expansion strut pair of chevron-shape in a first expansion column are within the scope of a tubular stent of present invention.

A first expansion strut pair first corner is formed where the first joining strut is coupled to the first expansion strut of chevron-shape, and a first expansion strut pair second corner is formed where the first joining strut is coupled to the second expansion strut of chevron-shape. A second expansion strut pair first corner is formed where the second joining strut is coupled to the second expansion strut of chevron-shape, and a second expansion strut pair second corner is formed where the second joining strut is coupled to the third expansion strut of chevron-shape. A third expansion strut pair first corner is formed where the third joining strut is coupled to the third expansion strut of chevron-shape, and a third expansion strut pair second corner is formed where the third joining strut is coupled to the fourth expansion strut of chevron-shape. A fourth expansion strut pair first corner is formed where the fourth joining strut is coupled to the fourth expansion strut of chevron-shape, and a fourth expansion strut pair second corner is formed where the fourth joining strut is coupled to the fifth expansion strut. This process of forming the first and second corner in a first expansion strut pair is repeated until all the expansion strut pairs in a first expansion column are joined with their respective joining struts to form the first and second corners for each of the closed loop expansion strut pairs.

A second expansion column consists of a plurality of second expansion strut pairs of generally a chevron-shape in upright position with the vertex of chevron pointing upward. A first expansion strut pair in a second expansion column includes a first expansion strut of a chevron-shape, which has a stepped-apex configuration at the center and is dissimilar to a second expansion strut configuration, adjacent to a second expansion strut of a chevron-shape with a simple-apex. A first joining strut couples the first and second expansion struts of chevron-shape at a distal end of a first expansion strut pair to form a closed loop. When a first expansion strut pair is joined by a first joining strut to form a closed loop, a chevron-shaped slot is formed inside the first expansion strut pair, with a narrower slot width in the closed-loop end half and a wider slot width in the open end half, due to the dissimilar chevron-shapes of the first and second first expansion struts of a first expansion strut pair. A second expansion strut pair includes a third expansion strut of chevron-shape, which has a stepped-apex configuration at the center and is dissimilar to the second expansion strut configuration, adjacent to a second expansion strut of chevron-shape with a simple-apex. A second joining strut couples the second and third expansion struts at a proximal end of the second expansion strut pair to form a closed loop. When a second expansion strut pair is joined by a second joining strut to form a closed loop, a chevron-shaped slot is formed inside the second expansion strut pair, with a narrower slot width in the closed-loop end half and a wider slot width in the open end half, due to the dissimilar chevron-shapes of the second and third expansion struts of a second expansion strut pair. A third expansion strut pair includes a fourth expansion strut of chevron-shape adjacent to the third expansion strut of chevron-shape, which has a stepped-apex configuration at the center and is dissimilar to the fourth expansion strut configuration. A third joining strut couples the third and fourth expansion struts at a distal end of the third expansion strut pair to form a closed loop. When a third expansion strut pair is joined by a third joining strut to form a closed loop, a chevron-shaped slot is formed inside the third expansion strut pair, with a narrower slot width in the closed-loop end half and a wider slot width in the open end half, due to the dissimilar chevron-shapes of the third and fourth expansion struts of a third expansion strut pair. A fourth expansion strut pair includes a fifth expansion strut of chevron-shape, which has a stepped-apex configuration at the center, adjacent to a fourth expansion strut of chevron-shape with a simple-apex. A fourth joining strut couples the fourth and fifth expansion struts at a proximal end of the fourth expansion strut pair. When a fourth expansion strut pair is joined by a fourth joining strut to form a closed loop, a chevron-shaped slot is formed inside the fourth expansion strut pair, with a narrower slot width in the closed-loop end half and a wider slot width in the open end half, due to the dissimilar chevron-shapes of the fourth and fifth expansion struts of a fourth expansion strut pair. These expansion strut pairs of two dissimilar chevron-shape coupled by a joining struts to form a closed loop in an alternating proximal or distal end of the expansion strut pairs can be repeated to make the prescribed number of continuos chain of expansion strut pairs in a second expansion column around the circumference in an unbroken fashion in a tubular stent of present invention. A set of two consecutive chevron-shaped expansion strut pairs in an unbroken sequence is called expansion strut cycles. In this application, the illustrations contain six (6) chevron-shaped expansion strut pair cycles or twelve (12) chevron-shaped expansion strut pairs in a second expansion column in the 2-dimensional cut-open drawings. However, the number of chevron-shaped expansion strut pairs or expansion strut pair cycles in a second expansion column can variably be changed according to the application requirements of the specific stent made of present invention. The variation of the number of expansion strut pairs or expansion pair cycles in a second expansion column is within the scope of a tubular stent of present invention.

Although the illustrations in this application shows only a neutrally arranged upright expansion strut pairs of chevron-configuration within the first, second or third expansion strut columns; the expansion strut pairs of chevron-shape can be arranged in any tilted angulation within their assigned expansion columns. The first and second expansion struts of chevron-shape in a first expansion strut pair in a second expansion column are parallel to each other, but the first and second expansion struts of chevron-shape in a first expansion strut pair in a second expansion column do not parallel to the longitudinal axis of the tubular stent. However, the first and second expansion struts of chevron-shape in a first expansion strut pair in a second expansion column do not have to parallel to each other. Both the parallel and non-parallel arrangement of the first and second expansion struts of chevron-shape in a first expansion strut pair in a second expansion column is within the scope of this invention. The first and second expansion struts of chevron-shape in a first expansion strut pair in a second expansion column can be made of dissimilar chevron patterns as shown in the illustrations of this provisional application. However, the first and second expansion struts of chevron-shape in a first expansion strut pair in a second expansion column can be made of similar chevron-shapes; the first and second expansion struts in a first expansion strut pair may consists of two simple straight chevron-shape struts or the first and second expansion struts in a first expansion strut pair may consists of two stair-step chevron-shape struts. Any other variations of basic chevron configuration of similar or dissimilar combination in a first expansion strut pair of chevron-shape in a second expansion column are within the scope of a tubular stent of present invention.

A first expansion strut pair first corner is formed where the first joining strut is coupled to the first expansion strut of chevron-shape, and a first expansion strut pair second corner is formed where the first joining strut is coupled to the second expansion strut of chevron-shape. A second expansion strut pair first corner is formed where the second joining strut is coupled to the second expansion strut of chevron-shape, and a second expansion strut pair second corner is formed where the second joining strut is coupled to the third expansion strut of chevron-shape. A third expansion strut pair first corner is formed where the third joining strut is coupled to the third expansion strut of chevron-shape, and a third expansion strut pair second corner is formed where the third joining strut is coupled to the fourth expansion strut of chevron-shape. A fourth expansion strut pair first corner is formed where the fourth joining strut is coupled to the fourth expansion strut of chevron-shape, and a fourth expansion strut pair second corner is formed where the fourth joining strut is coupled to the fifth expansion strut. This process of forming the first and second corner in a first expansion strut pair is repeated until all the expansion strut pairs in a first expansion column are joined with their respective joining struts to form the first and second corners for each of the closed loop expansion strut pair.

A first connecting strut column is formed of a plurality of first connecting struts of roughly symmetrical M-frame shape in upright position. A first connecting strut of the first connecting strut column includes a connecting strut proximal section, a connecting strut distal section and a connecting strut intermediate section. A first connecting strut proximal section has two portions; a short stem that is coupled at a perpendicular or slant angle to the outer side of the distal end of a second expansion strut of second expansion strut pair of first expansion column, and a proximal long portion that is coupled to the first short stem proximally and to the intermediate section distally. The proximal long part generally parallels to the longitudinal axis of the tubular stent, although the proximal long portion can be parallel to the distal half of a second expansion strut of chevron-shape of second expansion strut pair of first expansion column or non-parallel to the longitudinal axis of the tubular stent, as alternative configurations. A first connecting strut distal section also has two parts; a short stem that is coupled at a perpendicular or slant angle to the outer side of the proximal end of a second expansion strut of second expansion strut pair of second expansion column, and a distal long portion that is coupled to the first short stem distally and to the intermediate section proximally. The distal long portion generally parallels to the longitudinal axis of the tubular stent, although the distal long portion can be parallel to the proximal half of a second expansion strut of chevron-shape of second expansion strut pair in a second expansion column or non-parallel to the longitudinal axis of the tubular stent, as alternative configurations. A first connecting strut proximal section and a first connecting strut distal section are ipsilateral mirror images to each other, with their terminal ends both pointing downward in a same direction as they attach to their respective ipsilateral attachment sites on the outer side of the apposed closed loop chevron strut pairs.

A first connecting strut intermediate section also has a generally symmetrical configuration. A first connecting strut intermediate section is a symmetrical upside down trapezoid slot or loop configuration with slanted slopes on each side and flat horizontal bottom in the valley. A proximal end of proximal slanted slope of the upside down trapezoid intermediate section is connected to a distal end of the proximal long portion of a first connecting strut proximal section. A distal end of distal slanted slope of the upside down trapezoid intermediate section is connected to a proximal end of the distal long portion of a first connecting strut distal section. The upside down trapezoid valley of an M-shaped intermediate section of a first connecting strut in a first connecting column is positioned in the inter-space between the second closed expansion strut pair in a first expansion column and the second closed expansion strut pair in a second expansion column. In other words, the central part, a upside down trapezoidal intermediate section that form a slot or closed loop, of the M-frame connector does not protrude out into the central area of a stent cell space formed in the tubular stent. In this configuration, the trapezoidal intermediate section of an M-shaped first connecting strut divides the connecting space between the two apposed expansion columns into three (3) separate spaces or looped compartments. However, the position of a upside down trapezoidal intermediate section of an M-shaped first connecting strut can have a reverse upright position without modifying the configuration of a connecting strut proximal section or distal section, protruding out of the inter-space between the two apposed closed-loop expansion strut pairs, instead of a former position in between the two apposed closed-loop expansion strut pairs. This variation of the position and orientation of the intermediate section in an M-shaped first connecting strut in a first connecting column is within the scope of present invention.

An M-shaped first connecting strut in a first connecting strut column is attached to the ipsilateral outer sides of the two apposed closed-loop strut pairs in a first expansion column and a second expansion column. A short stem of proximal section of a first connecting strut in a first connecting column is attached to the ipsilateral outer side of a distal end of a second expansion strut of a second expansion strut pair of chevron shape in a first expansion column, and a short stem of distal section of the first connecting strut in a first connecting column is attached to the ipsilateral outer side of a proximal end of a second expansion strut of a second expansion strut pair of chevron shape in a second expansion column. Both the proximal end and distal end of a first connecting strut in a first connecting column point downward to attach to the upper outer ipsilateral sides of the two apposed closed-loop strut pairs of the first and second expansion columns. Each of six (6) M-frame connecting struts in a first connecting column connects the first expansion column to the second expansion column in a manner identical to the first connecting strut in the first connecting column as described foregoing, in an unbroken chain-mesh pattern around the circumference of the tubular stent. The number of connecting struts in a first connecting strut column can be changed to more or less number than six (6), according to the prescribed demand of a tubular stent made of present invention. Variations in number of M-frame connecting struts in a first connecting column is within the scope of a tubular stent of present invention. Likewise, skipping of the connection of an M-shaped first connecting strut between the two apposed expansion columns can be made. This skipping of interconnection with the M-shaped first connecting strut between the two companion expansion columns is within the scope of present invention.

In the main illustrations, there are six (6) M-frame connectors in a first connector column coupling the first and second expansion columns, with all the M-frame connectors assuming up-right positions. However, the position of first M-shaped connecting struts in a first connecting column can have a mixture of some in upright positions and some in upside down positions. By mixing upright and upside down positions of the M-shaped connecting struts in a first connecting column can enhance a certain flexibility and performance characteristics. A mixing pattern of three consecutive up-right and three consecutive up-side down positions of the M-frame connectors in a first connecting column could change the flexibility and trackability characteristics of a tubular stent of present invention. Variability of the M-frame connector attachment pattern and orientation is within the scope of a tubular stent of present invention. Another key feature of an M-frame connector is a variable connector width. In most coronary application, an M-frame connector width would be narrower than a width of a closed-loop expansion strut pair, where an M-frame connector is ipsilaterally attached. However, a width of an M-frame connector could be made same or wider than a width of a closed-loop expansion strut pair, where an M-frame connector is ipsilaterally attached.

A third expansion column consists of a plurality of third expansion strut pairs of generally a chevron-shape in upright position with the vertex of the chevron pointing upward. A first expansion strut pair includes a first expansion strut of a chevron-shape with a simple-apex, adjacent to a second expansion strut of a chevron-shape, which has a stepped-apex configuration at the center and is dissimilar to the first expansion strut configuration. A first joining strut couples the first and second expansion struts of chevron-shape at a proximal end of a first expansion strut pair to form a closed loop. When a first expansion strut pair is joined by a first joining strut to form a closed loop, a chevron-shaped slot is formed inside the first expansion strut pair, with a narrower slot width in the closed-end half and a wider slot width in the open-end half, due to the dissimilar chevron-shapes of the first and second first expansion struts of a first expansion strut pair. A second expansion strut pair includes a third expansion strut of chevron-shape, adjacent to a second expansion strut of chevron-shape with a simple-apex, which has a stepped-apex configuration at the center and is dissimilar to the second expansion strut configuration. A second joining strut couples the second and third expansion struts at a distal end of the second expansion strut pair to form a closed loop. When a second expansion strut pair is joined by a second joining strut to form a closed loop, a chevron-shaped slot is formed inside the second expansion strut pair, with a narrower slot width in the closed-end half and a wider slot width in the open-end half, due to the dissimilar chevron-shapes of the second and third expansion struts of a second expansion strut pair. A third expansion strut pair includes a fourth expansion strut of chevron-shape, which has a stepped-apex configuration at the center and is dissimilar to the third expansion strut configuration, adjacent to a third expansion strut of chevron-shape with a simple-apex. A third joining strut couples the third and fourth expansion struts at a proximal end of the third expansion strut pair to form a closed loop. When a third expansion strut pair is joined by a third joining strut to form a closed loop, a chevron-shaped slot is formed inside the third expansion strut pair, with a narrower slot width in the closed-end half and a wider slot width in the open-end half, due to the dissimilar chevron-shapes of the third and fourth expansion struts of a third expansion strut pair. A fourth expansion strut pair includes a fifth expansion strut of chevron-shape with a simple-apex, adjacent to a fourth expansion strut of chevron-shape, which has a stepped-apex configuration at the center and is dissimilar to the fourth expansion strut configuration. A fourth joining strut couples the fourth and fifth expansion struts at a distal end of the fourth expansion strut pair. When a fourth expansion strut pair is joined by a fourth joining strut to form a closed loop, a chevron-shaped slot is formed inside the fourth expansion strut pair, with a narrower slot width in the closed-end half and a wider slot width in the open-end half, due to dissimilar chevron-shapes of the fourth and fifth expansion struts of a fourth expansion strut pair. These expansion strut pairs of two dissimilar chevron-shape coupled by a joining struts to form a closed loop at an alternating proximal or distal end of the expansion strut pairs can be repeated to make the prescribed number of expansion strut pairs in an unbroken fashion around the circumference in a tubular stent of present invention. A set of two consecutive chevron-shaped expansion strut pairs in an unbroken sequence is called expansion strut cycles. In this application, the illustrations contain six (6) chevron-shaped expansion strut pair cycles or twelve (12) chevron-shaped expansion strut pairs in a third expansion column in the 2-dimensional cut-open drawings. However, the number of chevron-shaped expansion strut pairs or expansion strut pair cycles in a third expansion column can variably be changed according to the application requirements of the specific stent made of present invention. Variation of the number of expansion strut pairs or expansion strut pair cycles in a third expansion column is within the scope of a tubular stent of present invention.

Although the illustrations in this application shows only a neutrally arranged upright expansion strut pairs of chevron-configuration within the first, second or third expansion strut columns; the expansion strut pairs of chevron-shape can be arranged in any tilted angulation within their assigned expansion columns. The first and second expansion struts of chevron-shape in a first expansion strut pair in a third expansion column are parallel to each other, but the first and second expansion struts of chevron-shape in a first expansion strut pair in a third expansion column do not parallel to the longitudinal axis of the tubular stent. However, the first and second expansion struts of chevron-shape in a first expansion strut pair in a third expansion column do not have to parallel to each other. Both the parallel and non-parallel arrangement of the first and second expansion struts of chevron-shape in a first expansion strut pair in a third expansion column is within the scope of a tubular stent of present invention.

The first and second expansion struts of chevron-shape in a first expansion strut pair in a third expansion column can be made of dissimilar chevron patterns as shown in the illustrations of this provisional application. However, the first and second expansion struts of chevron-shape in a first expansion strut pair in a third expansion column can be made of similar chevron-shapes; the first and second expansion struts in a first expansion strut pair may consists of two chevron-shape struts of simple-apex or the first and second expansion struts in a first expansion strut pair may consists of two chevron-shape struts of stepped-apex. Any other variations of basic chevron configuration of similar or dissimilar combination in a first expansion strut pair in a third expansion column are within the scope of chevron-shape expansion strut configuration of a tubular stent of present invention.

A first expansion strut pair first corner is formed where the first joining strut is coupled to the first expansion strut of chevron-shape, and a first expansion strut pair second corner is formed where the first joining strut is coupled to the second expansion strut of chevron-shape. A second expansion strut pair first corner is formed where the second joining strut is coupled to the second expansion strut of chevron-shape, and a second expansion strut pair second corner is formed where the second joining strut is coupled to the third expansion strut of chevron-shape. A third expansion strut pair first corner is formed where the third joining strut is coupled to the third expansion strut of chevron-shape, and a third expansion strut pair second corner is formed where the third joining strut is coupled to the fourth expansion strut of chevron-shape. A fourth expansion strut pair first corner is formed where the fourth joining strut is coupled to the fourth expansion strut of chevron-shape, and a fourth expansion strut pair second corner is formed where the fourth joining strut is coupled to the fifth expansion strut. This process of forming the first and second corner in a first expansion strut pair is repeated until all the expansion strut pairs in a first expansion column are joined with their respective joining struts to form the first and second corners for each of the closed loop expansion strut pair.

A second connecting strut column is formed of a plurality of second connecting struts of roughly symmetrical M-frame shape in upside down position. A first connecting strut of the first connecting strut column includes a connecting strut proximal section, a connecting strut distal section and a connecting strut intermediate section. A first connecting strut proximal section has two parts; a short stem that is coupled at a perpendicular or slant angle to the lower outer side of the distal end of a second expansion strut of first expansion strut pair in a second expansion column, and a proximal long portion that is coupled to the proximal short stem proximally and to the intermediate section distally. The proximal long portion generally parallels to the longitudinal axis of the tubular stent, although the proximal long portion can be parallel to the distal half of a second expansion strut of chevron-shape of first expansion strut pair in a second expansion column, or non-parallel to the longitudinal axis of the tubular stent, as alternative configurations. A first connecting strut distal section also has two parts; a short stem that is coupled at a perpendicular or slant angle to the lower outer side of the proximal end of a second expansion strut of first expansion strut pair in a third expansion column, and a distal long portion that is coupled to the short stem distally and to the intermediate section proximally. The second long part generally parallels to the longitudinal axis of the tubular stent, although the second long part can be parallel to the proximal half of a second expansion strut of chevron-shape of first expansion strut pair in a third expansion column, or non-parallel to the longitudinal axis of the tubular stent, as alternative configurations. A first connecting strut proximal section and a first connecting strut distal section are ipsilateral mirror images to each other, with their terminal ends both pointing upward as they attach to their respective ipsilateral attachment sites on the lower outside of the apposed closed loop chevron strut pairs in two adjacent second and third expansion columns.

A first connecting strut intermediate section has a generally symmetrical configuration. A first connecting strut intermediate section is a symmetrical upright trapezoidal configuration with slanted slopes on each side and flat horizontal plateau at the top. A proximal end of proximal slant slope of the upright trapezoidal intermediate section is connected to a distal end of the proximal long portion of a first connecting strut proximal section. A distal end of distal slant slope of the upright trapezoidal intermediate section is connected to a proximal end of the distal long portion of a first connecting strut distal section. The trapezoidal looped intermediate section of an M-shaped first connecting strut in a second connecting column is positioned in the interconnecting-space between the first closed loop expansion strut pair in a second expansion column and the first closed loop expansion strut pair in a third expansion column. In this configuration, the trapezoidal intermediate section of an M-shaped first connecting strut divides the connecting space between the two apposed expansion columns into three (3) separate spaces or looped compartments. In other words, an upright looped trapezoidal intermediate section of a first M-frame connector in a second connecting column does not protrude out into the central area of a stent cell space formed in the tubular stent. However, the position of a trapezoidal intermediate section of an M-shaped first connecting strut can have a reverse upside down position without modifying the configuration of a first connecting strut proximal section or distal section, protruding out of the inter-space between the two apposed closed-loop expansion strut pairs, out into the central cell space. Variations of position and orientation of the trapezoidal intermediate section in an M-shaped first connecting strut in a second connecting column is within the scope of M-shaped connecting strut of the stent of present invention.

The terminal ends of an M-shaped first connecting strut in a second connecting strut column is attached to the lower ipsilateral outer sides of the two apposed closed-loop strut pairs in a second expansion column and a third expansion column. A short stem of proximal section of a first connecting strut in a second connecting column is attached to the lower ipsilateral outer side of a distal end of a second expansion strut of a first expansion strut pair of chevron shape in a second expansion column, and a short stem of distal section of the first connecting strut in a second connecting column is attached to the lower ipsilateral outer side of a proximal end of a second expansion strut of a first expansion strut pair of chevron shape in a third expansion column. Both the proximal end and distal end of an M-frame first connecting strut in a second connecting column point upward to attach to the lower outer ipsilateral sides of the two apposed closed-loop strut pairs of the second and third expansion columns. Each of six (6) M-frame connecting struts in a second connecting column connects the second expansion column to the third expansion column in a manner identical to the first connecting strut in the second connecting strut column as described foregoing, in an unbroken chain-mesh pattern around the circumference of the tubular stent. The number of connecting struts in a second connecting strut column can be changed to more or less number than six (6), according to the prescribed demand of a tubular stent made of present invention. Variations in number of M-frame connecting struts in a second connecting column is within the scope of a tubular stent of present invention. Likewise, skipping of the connection of an M-shaped first connecting strut between the two apposed expansion columns can be made. This skipping of interconnection with the M-shaped first connecting strut between the two companion expansion columns are within the scope of present invention.

In the main illustrations, there are six M-frame connectors in a second connector column coupling the second and third expansion columns, with all the M-frame connectors assuming upside down positions. However, the position of first M-shaped connecting struts in a second connecting column can have a mixture of some in upright position and some in upside down position. By mixing upright and upside down positions of the M-shaped connecting struts in a second connecting column can enhance certain flexibility and performance characteristics of the stent made of present invention. A mixing pattern of three consecutive upright and three consecutive upside down positions of the M-frame connectors in a second connecting column could change the flexibility and trackability characteristics of a tubular stent of present invention. Variability of the M-frame connector attachment and orientation pattern is within the scope of a tubular stent of present invention. Another key feature of an M-frame connector is a variable connector width. In most coronary application, an M-frame connector width would be narrower than a width of a closed-loop expansion strut pair, where an M-frame connector is ipsilaterally attached. However, a width of an M-frame connector could be made same or wider than a width of a closed-loop expansion strut pair, where an M-frame connector is ipsilaterally attached.

DETAILED DESCRIPTION OF THE DRAWINGS

Figure 1:
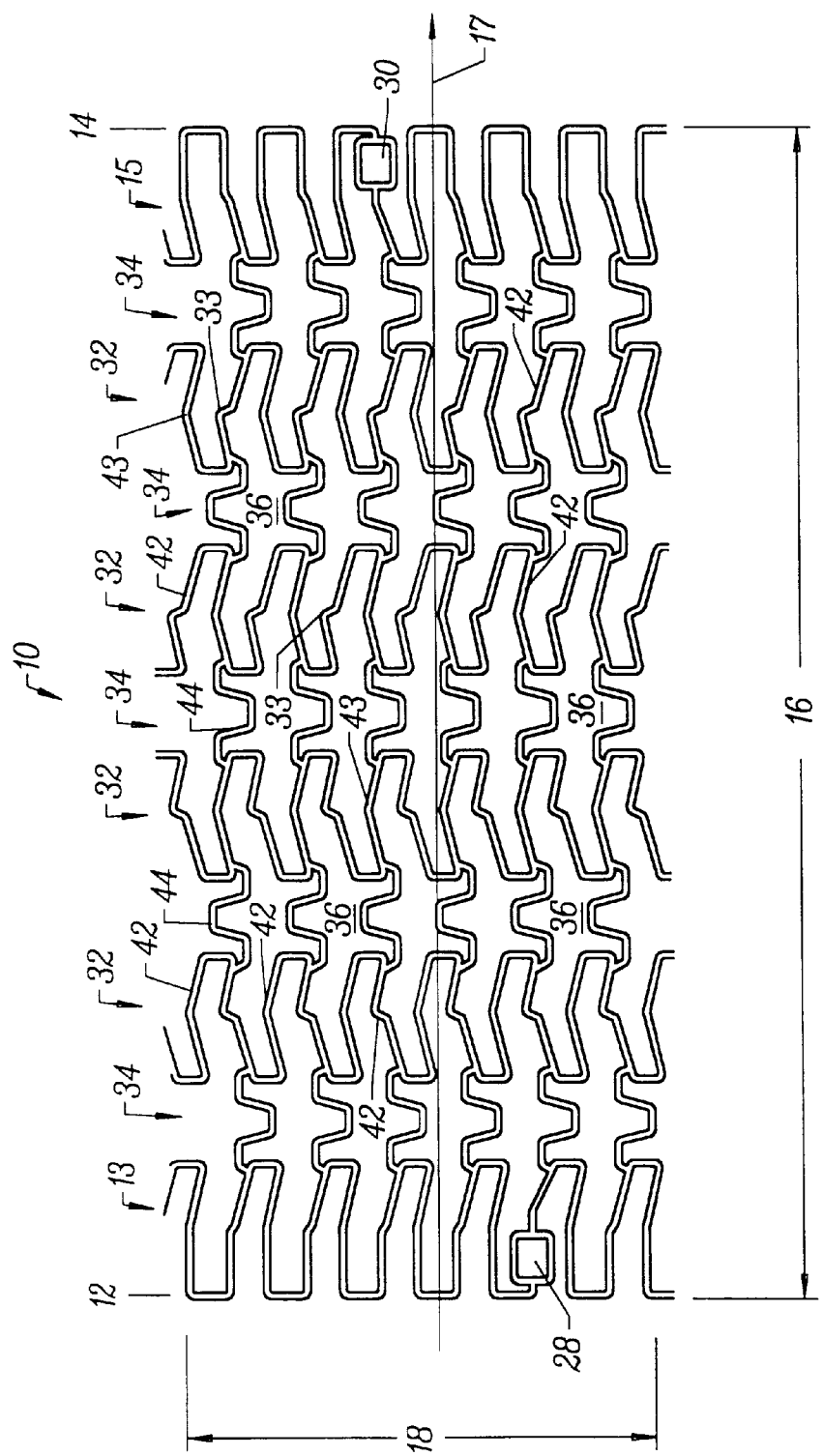
FIG. 1—A 2-dimentional cut-open schematic drawing of a short version of a tubular stent of present invention.

FIG. 1—The stent 10 is illustrated in a cut-open 2-dimensional schematic drawing with the longitudinal axis 17 and the longitudinal length 16 aligned horizontally, and the circumferential dimension 18 aligned vertically. The proximal end 12 is defined by the proximal edges of the horizontal half of the expansion struts 42 and their respective joining struts 46 of the proximal expansion column 13, and the distal end 14 is defined by the distal edges of the horizontal half of the expansion struts 42 and their respective joining struts 46 of the distal expansion column 15. The expansion struts 42 in the proximal expansion column 13 has a modified chevron configuration. The proximal half of the individual expansion struts 42 has a horizontally paralleling strut configuration, whereas the distal half of the individual expansion struts 42 has a slanted paralleling strut 42 configuration, similar to the chevron-shaped expansion struts 42 in the expansion columns between the proximal 13 and distal 15 expansion columns. Both the proximal 13 and distal 15 expansion columns have the marker buttons 28 and 30 respectively in their expansion columns 13 and 15.

Figure 2:
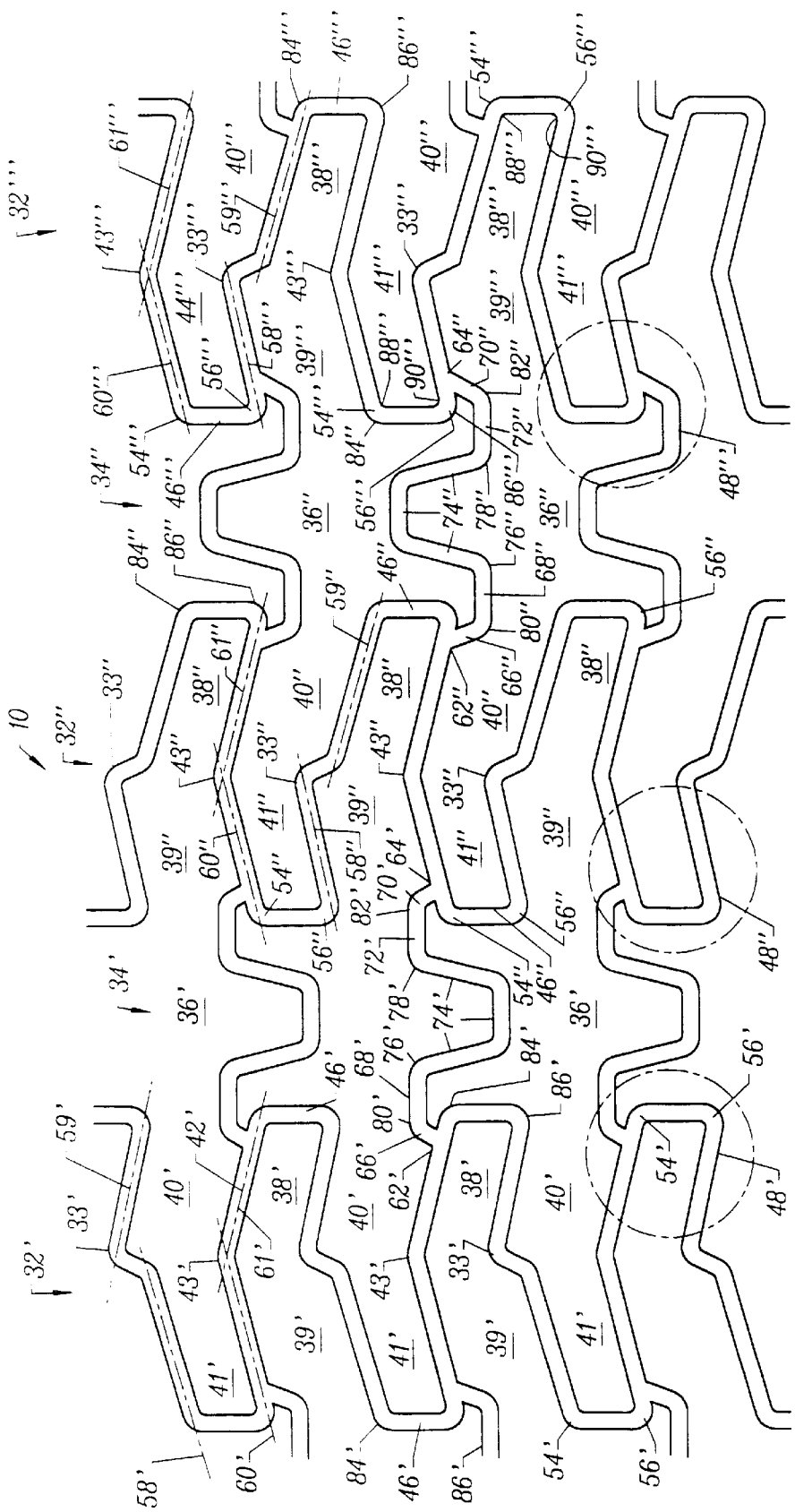
FIG. 2—The FIG. 1 above is magnified to mark the details of the stent strut configuration and the stent cell geometry.
Figure 3:
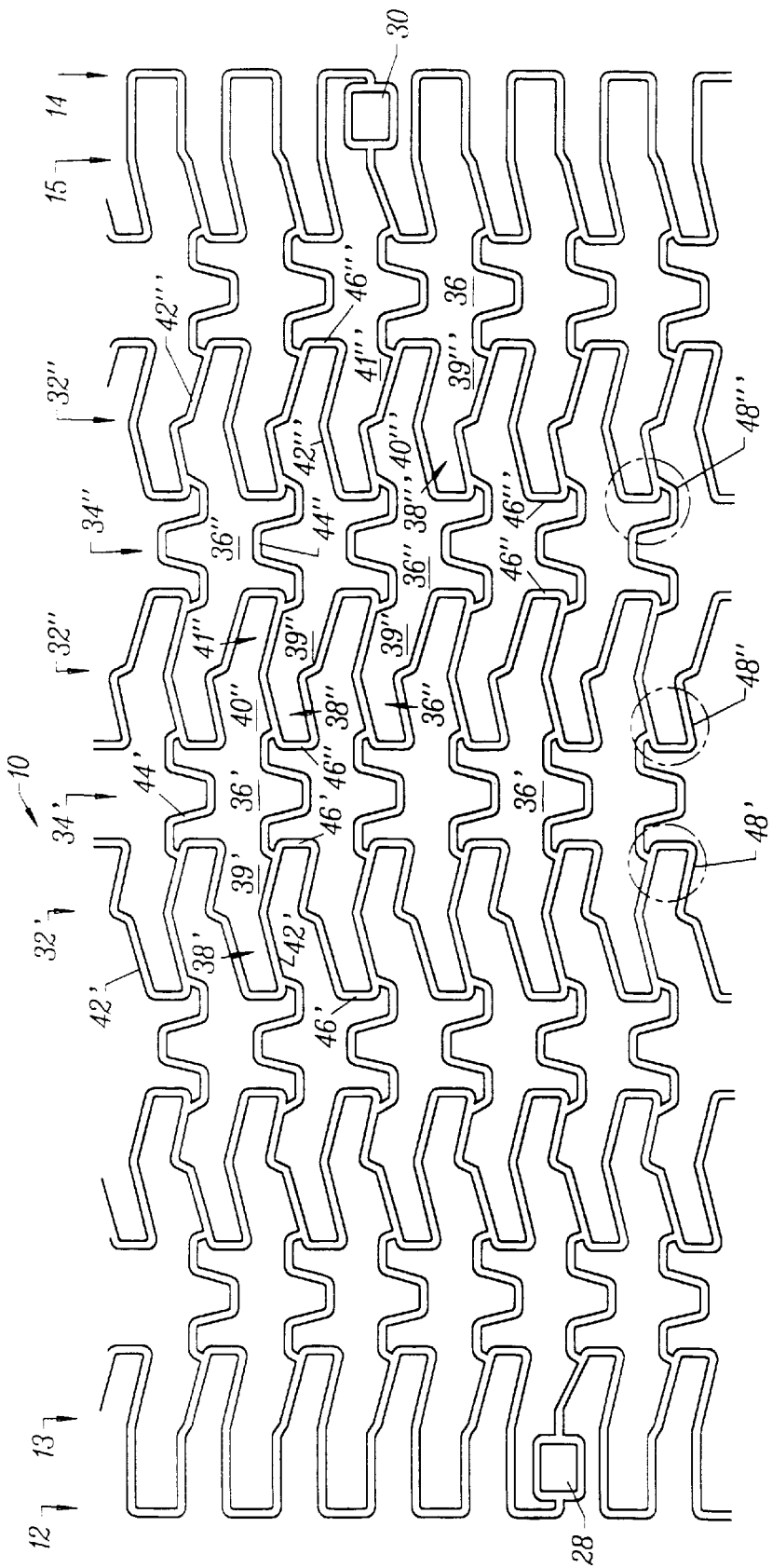
FIG. 3—Another magnified view of FIG. 1 above to illustrate the expansion columns and connecting columns and how they are inter connected to form a continuous chain-mesh strut configuration of a tubular stent of present invention.

FIG. 2—This figure is a magnified view of the details of the strut configurations of the stent 10. FIG. 3 has a complete view of the entire stent 10 like FIG. 1. In the following detailed description of the drawings, both FIG. 2 and FIG. 3 would be used commingling to better facilitate the description of the stent 10.

A first expansion column 32' includes of a plurality of first expansion strut 42' pairs of chevron-shape in upright position with the apices 33' and 43' of chevron pointing upward. A first expansion strut 42' pair includes a first expansion strut 42' of generally a chevron-shape, which has a stepped-apex configuration at the center and is dissimilar to a second expansion strut 42' configuration, adjacent to a second expansion strut 42' of generally a chevron-shape with a simple-apex. A first joining strut 46' couples the first and second expansion struts 42' of chevron-shape at a proximal end of a first expansion strut 42' pair to form a closed loop 48'. When a first expansion strut 42' pair is joined by a first joining strut 46' to form a closed loop 48', a chevron-shaped slot is formed inside the first expansion strut 42' pair, with a narrower slot width in the closed loop half 41' and a wider slot width in the open-end half 40' due to the dissimilar chevron-shapes of the first and second first expansion struts 42' of a first expansion strut 42' pair. A second expansion strut 42' pair includes a third expansion strut 42' of chevron-shape, which has a stepped-apex configuration at the center and is dissimilar to a second expansion strut 42' configuration, adjacent to a second expansion strut 42' of chevron-shape with a simple-apex. A second joining strut 46' couples the second and third expansion struts 42' at a distal end of the second expansion strut 42' pair to form a closed loop 48'. When a second expansion strut 42' pair is joined by a second joining strut 46' to form a closed loop 48', a chevron-shaped slot is formed inside the second expansion strut 42' pair, with a narrower slot width in the closed-loop half 38' and a wider slot width in the open-end half 39', due to the dissimilar chevron-shapes of the second and third expansion struts 42' of a second expansion strut 42' pair. A third expansion strut 42' pair includes a fourth expansion strut 42' of chevron-shape with a simple-apex adjacent to the third expansion strut 42' of chevron-shape, which has a stepped-apex configuration at the center and is dissimilar to a third expansion strut 42' configuration. A third joining strut 46' couples the third and fourth expansion struts 42' at a proximal end of the third expansion strut 42' pair to form a closed loop 48'. When a third expansion strut 42' pair is joined by a third joining strut 46' to form a closed loop 48', a chevron-shaped slot is formed inside the third expansion strut 42' pair, with a narrower slot width in the closed-loop half 41' and a wider slot width in the open-end half 40', due to the dissimilar chevron-shapes of the third and fourth expansion struts 42' of a third expansion strut 42' pair. A fourth expansion strut 42' pair includes a fifth expansion strut 42' of chevron-shape, which has a stepped-apex configuration at the center and is dissimilar to a fourth expansion strut 42' configuration, adjacent to a fourth expansion strut 42' of chevron-shape with a simple-apex. A fourth joining strut 46' couples the fourth and fifth expansion struts at a distal end of the fourth expansion strut 42' pair. When a fourth expansion strut 42' pair is joined by a fourth joining strut 46' to form a closed loop 48', a chevron-shaped slot is formed inside the fourth expansion strut 42' pair, with a narrower slot width in the closed-loop half 38' and a wider slot width in the open-end half 39', due to the dissimilar chevron-shapes of the fourth and fifth expansion struts 42' of a fourth expansion strut 42' pair. These expansion strut 42' pairs of two dissimilar chevron-shape coupled by a joining strut 46' to form a closed loop 48' in an alternating proximal or distal end of the expansion strut 42' pairs can be repeated to make the prescribed number of continuos chain of expansion strut 42' pairs around the circumference 18 in an unbroken fashion in the stent 10 of present invention. A set of two consecutive chevron-shaped expansion strut 42' pairs in an unbroken sequence is called expansion strut 42' cycles. In this application, FIGS. 1 and 3 contain six (6) chevron-shaped expansion strut 42' pair cycles or twelve (12) chevron-shaped expansion strut 42' pairs in a first expansion column 32' in the 2-dimensional cut-open drawings. However, the number of chevron-shaped expansion strut 42' pair or expansion strut 42' pair cycle in a first expansion column 32' can variably be changed according to the application requirements of the specific stent 10 made of present invention. The variation of the number of expansion strut 42' pair or expansion strut 42' pair cycle in a first expansion column 32' is within the scope of a tubular stent 10 of present invention.

Although FIGS. 1, 2, and 3 in this application shows only a neutrally arranged up-right expansion strut 10 pairs of chevron-configuration within the first 32', second 32" or third 32'" expansion strut columns; the expansion strut 42 pairs of chevron-configuration can be arranged in any tilted angulation within their assigned expansion columns 32. The first and second expansion struts 42' of chevron-shape in a first expansion strut 42' pair are parallel to each other, but the first and second expansion struts 42' of chevron-shape in a first expansion strut 42' pair do not parallel to the longitudinal axis 17 of the tubular stent 10. The proximal or distal half of a first expansion strut pair in the first expansion column can be arranged to parallel to the longitudinal axis of the stent. Such an arrangement would also change the axis of the connecting tem of the connector strut between the two companion expansion columns. However, the first and second expansion struts 42' of chevron-shape in a first expansion strut 42' pair do not have to parallel to each other, either. Both the parallel and non-parallel arrangement of the first and second expansion struts 42' of chevron-shape in a first expansion strut 42' pair in a tubular stent 10 is within the scope of present invention. In further amplifying these strut alignment details, the expansion strut 42' pair can be elaborated further. In a pair of chevron-shaped expansion struts 42', the chevron configuration with a simple-apex such as the second expansion strut 42' of the first expansion strut 42' pair in a first expansion column 32' has two axes 60' and 61' divided at the center by a simple-apex 43'; whereas the chevron configuration with stepped-apex such as the second expansion strut 42' of the first expansion strut 42' pair in a first expansion column 32' has two axes 58' and 59' divided at the center by a stepped apex 33'. In FIGS. 1 and 2, the axes 58' and 60' parallel to each other but they 58', 60' do not parallel to the longitudinal axis 17 of a tubular stent 10. However, the expansion strut axes 58' and 60' do not have to parallel to each other. Likewise, the axes 59' and 61' of the first expansion strut 42' pair parallel to each other but they 59', 61' do not parallel to the longitudinal axis 17 of a tubular stent 10. However, the expansion strut axes 59' and 61' do not have to parallel to each other.

The first and second expansion struts 42' of chevron-shape in a first expansion strut 42' pair in a first expansion column 32' can be made of two dissimilar chevron patterns as shown in FIGS. 1, 2 and 3 of this provisional application. However, the first and second expansion struts 42' of chevron-shape in a first expansion strut 42' pair in a first expansion column 32' can be made of similar chevron-shapes; the first and second expansion struts 42' in a first expansion strut 32' pair may consists of two chevron-shape struts 42' with a simple-apex or the first and second expansion struts 42' in a first expansion strut 42' pair may consists of two chevron-shape struts 42' with a stepped-apex. Any other variations of basic chevron configuration of similar or dissimilar combination in a first expansion strut 42' pair of chevron-shape in a first expansion column 32' are within the scope of a tubular stent 10 of present invention.

A first expansion strut 42' pair first corner 54' is formed where the first joining strut 46' is coupled to the first expansion strut 42' of chevron-shape, and a first expansion strut 42' pair second corner 56' is formed where the first joining strut 46' is coupled to the second expansion strut 42' of chevron-shape. A second expansion strut 42' pair first corner 54' is formed where the second joining strut 46' is coupled to the second expansion strut 42' of chevron-shape, and a second expansion strut 42' pair second corner 56' is formed where the second joining strut 46' is coupled to the third expansion strut 42' of chevron-shape. A third expansion strut 42' pair first corner 54' is formed where the third joining strut 46' is coupled to the third expansion strut 42' of chevron-shape, and a third expansion strut 42' pair second corner 56' is formed where the third joining strut 46' is coupled to the fourth expansion strut 42' of chevron-shape. A fourth expansion strut 42' pair first corner 54' is formed where the fourth joining strut 46' is coupled to the fourth expansion strut 42' of chevron-shape, and a fourth expansion strut 42' pair second corner 56' is formed where the fourth joining strut 46' is coupled to the fifth expansion strut 42'. This process of forming the first 54' and second 56' corner in a first expansion strut 42' pair is repeated until all the expansion strut 42' pairs in a first expansion column 32' are joined with their respective joining struts 46' to form the first 54' and second 56' corners for each of the closed loop 48' expansion strut 42' pair.

A second expansion column 32" consists of a plurality of second expansion strut 42" pairs of generally a chevron-shape in upright position with the vertex of chevron pointing upward. A first expansion strut 42" pair includes a first expansion strut 42" of a chevron-shape, which has a stepped-apex configuration at the center and is dissimilar to a second expansion strut 42" configuration, adjacent to a second expansion strut 42" of a chevron-shape with a simple-apex. A first joining strut 46" couples the first and second expansion struts 42" of chevron-shape at a distal end of a first expansion strut 42" pair to form a closed loop 48". When a first expansion strut 42" pair is joined by a first joining strut 46" to form a closed loop 48'", a chevron-shaped slot is formed inside the first expansion strut 42" pair, with a narrower slot width in the closed-loop end half 38" and a wider slot width in the open-end half 39'", due to the dissimilar chevron-shapes of the first and second first expansion struts 42" of a first expansion strut 42" pair. A second expansion strut 42" pair includes a third expansion strut 24" of chevron-shape, which has a stepped-apex configuration at the center and is dissimilar to the second expansion strut 42" configuration, adjacent to a second expansion strut 42" of chevron-shape with a simple-apex. A second joining strut 46" couples the second and third expansion struts 42" at a proximal end of the second expansion strut 42" pair to form a closed loop 48". When a second expansion strut 42" pair is joined by a second joining strut 46" to form a closed loop 48", a chevron-shaped slot is formed inside the second expansion strut 42" pair, with a narrower slot width in the closed-loop end half 41" and a wider slot width in the open-end half 40", due to the dissimilar chevron-shapes of the second and third expansion struts 42" of a second expansion strut 42" pair. A third expansion strut 42" pair includes a fourth expansion strut 42" of chevron-shape with a simple-apex adjacent to the third expansion strut 42" of chevron-shape, which has a stepped-apex configuration at the center and is dissimilar to the fourth expansion strut 42" configuration. A third joining strut 46" couples the third and fourth expansion struts 42" at a distal end of the third expansion strut 42" pair to form a closed loop 48". When a third expansion strut 42" pair is joined by a third joining strut 46" to form a closed loop 48", a chevron-shaped slot is formed inside the third expansion strut 42" pair, with a narrower slot width in the closed-loop end half 38" and a wider slot width in the open-end half 39", due to the dissimilar chevron-shapes of the third and fourth expansion struts 42" of a third expansion strut 42" pair. A fourth expansion strut 42" pair includes a fifth expansion strut 42" of chevron-shape, which has a stepped-apex configuration at the center and is dissimilar to the fourth expansion strut 42" configuration, adjacent to a fourth expansion strut 42" of chevron-shape with a simple-apex. A fourth joining strut 46" couples the fourth and fifth expansion struts 42" at a proximal end of the fourth expansion strut 42" pair. When a fourth expansion strut 42" pair is joined by a fourth joining strut 46" to form a closed loop, a chevron-shaped slot is formed inside the fourth expansion strut 42" pair, with a narrower slot width in the closed-loop end half 41 " and a wider slot width in the open-end half 40", due to the dissimilar chevron-shapes of the fourth and fifth expansion struts 42" of a fourth expansion strut 42" pair. These expansion strut 42" pairs of two dissimilar chevron-shape coupled by a joining struts 46" to form a closed loop 48" in an alternating proximal or distal end of the expansion strut 42" pairs can be repeated to make the prescribed number of continuous chain of expansion strut 42" pairs in a second expansion column 32" around the circumference 18 in an unbroken fashion in a tubular stent 10 of present invention. A set of two consecutive chevron-shaped expansion strut 42" pairs in an unbroken sequence is called expansion strut 42" cycles. In this application, FIGS. 1 and 3 contain six (6) chevron-shaped expansion strut 42" pair cycles or twelve (12) chevron-shaped expansion strut 42" pairs in a second expansion column 32" in the 2-dimensional cut-open drawings. However, the number of chevron-shaped expansion strut 42" pairs or expansion strut 42" pair cycles in a second expansion column 32" can variably be changed according to the application requirements of the specific stent 10 made of present invention. The variation of the number of expansion strut 42" pairs or expansion strut 42" pair cycles in a second expansion column 32" is within the scope of a tubular stent 10 of present invention.

Although the illustrations in this application shows only a neutrally arranged upright expansion strut 42" pairs of chevron-configuration within the first 32', second 32" or third 32'" expansion strut columns; the expansion strut 42 pairs of chevron-shape can be arranged in any tilted angu-lation within their assigned expansion columns 32. The first and second expansion struts 42" of chevron-shape in a first expansion strut 42" pair in a second expansion column 32" are parallel to each other, but the first and second expansion struts 42" of chevron-shape in a first expansion strut 42" pair in a second expansion column 32" do not parallel to the longitudinal axis 17 of the tubular stent 10. The proximal or distal half of a first expansion strut pair in the second expansion column can be arranged to parallel to the longitudinal axis of the stent. Such an arrangement would also change the axis of the connecting tem of the connector strut between the two companion expansion columns. However, the first and second expansion struts 42" of chevron-shape in a first expansion strut 42" pair in a second expansion column 32" do not have to parallel to each other. Both the parallel and non-parallel arrangement of the first and second expansion struts 42" of chevron-shape in a first expansion strut 42" pair in a second expansion column 32" is within the scope of present invention. In further amplifying these strut alignment details, the expansion strut 42" pair can be further elaborated. In a pair of chevron-shaped expansion struts 42", the simple-apex chevron configuration such as the second expansion strut 42" of the first expansion strut 42" pair in a second expansion column 32" has two axes 60" and 61" divided at the center by a vertex 43"; whereas the stepped-apex chevron configuration such as the third expansion strut 42" of the second expansion strut 42" pair in a second expansion column 32" has two axes 58" and 59" divided at the center by a vertex 33". In FIG. 2 and 3, the axes 58" and 60" parallel to each other but they 58", 60" do not parallel to the longitudinal axis 17 of a tubular stent 10. However, the expansion strut 42" axes 58" and 60" do not have to parallel to each other. Likewise, the axes 59" and 61 " of the second expansion strut 42" pair parallel to each other but they 59", 61" do not parallel to the longitudinal axis 17 of a tubular stent 10. However, the expansion strut 42" axes 59" and 61" do not have to parallel to each other.

The first and second expansion struts 42" of chevron-shape in a first expansion strut 42" pair in a second expansion column 32" can be made of dissimilar chevron patterns as shown in the illustrations. However, the first and second expansion struts 42" of chevron-shape of a first expansion strut 42" pair in a second expansion column 32" can be made of similar chevron-shapes; the first and second expansion struts 42" in a first expansion strut 42" pair may consists of two simple-apex chevron-shape struts 42" or the first and second expansion struts 42" in a first expansion strut 42" pair may consists of two stepped-apex chevron-shape struts 42". Any other variations of basic chevron configuration of similar or dissimilar combination in a first expansion strut 42" pair of chevron-shape in a second expansion column 32" are within the scope of a tubular stent 10 of present invention.

A first expansion strut 42" pair first corner 54" is formed where the first joining strut 46" is coupled to the first expansion strut 42" of chevron-shape, and a first expansion strut 42" pair second corner 56" is formed where the first joining strut 46" is coupled to the second expansion strut 42" of chevron-shape. A second expansion strut 42" pair first corner 54" is formed where the second joining strut 46" is coupled to the second expansion strut 42" of chevron-shape, and a second expansion strut 42" pair second corner 56" is formed where the second joining strut 46" is coupled to the third expansion strut 42" of chevron-shape. A third expansion strut 42" pair first corner 54" is formed where the third joining strut 42" is coupled to the third expansion strut 42" of chevron-shape, and a third expansion strut 42" pair second corner 56" is formed where the third joining strut 46" is coupled to the fourth expansion strut 42" of chevron-shape. A fourth expansion strut 42" pair first corner 54" is formed where the fourth joining strut 46" is coupled to the fourth expansion strut 42" of chevron-shape, and a fourth expansion strut 42" pair second corner 56" is formed where the fourth joining strut 42" is coupled to the fifth expansion strut 42". This process of forming the first 54" and second 56" corner in a first expansion strut 42" pair is repeated until all the expansion strut 42" pairs in a second expansion column 32" are joined with their respective joining struts 46" to form the first 54" and second 56" corners for each of the closed loop 48" expansion strut 42" pair.

A first connecting strut column 34' is formed of a plurality of first connecting struts 44' of roughly symmetrical M-frame shape in upright position. A first connecting strut 44' of the first connecting strut column 34' includes a connecting strut proximal section, a connecting strut distal section and a connecting strut intermediate section 74'. A first connecting strut proximal section has two parts; a short stem 66' that is coupled with its proximal end 62' at a perpendicular or slant angle to the outer top side of the distal end of a second expansion strut 42' of second expansion strut 42' pair of first expansion column 32', and a proximal long portion 68' that is coupled to the first short stem 66' proximally and to the intermediate section 74' distally. The proximal long portion 68' generally parallels to the longitudinal axis 17 of the tubular stent 10, although the proximal long portion 68' can be parallel to the distal half of a second expansion strut 42' of chevron-shape of second expansion strut 42' pair of first expansion column 32' or non-parallel to the longitudinal axis 17 of the tubular stent 10, as alternative configurations. A first connecting strut distal section also has two parts; a distal short stem 70' that is coupled with its distal end 64' at a perpendicular or slant angle to the outer top side of the proximal end of a second expansion strut 42" of second expansion strut 42" pair in a second expansion column 32", and a distal long portion 72' that is coupled to the distal short stem 70' distally and to the intermediate section 74' proximally. The distal long portion 72' generally parallels to the longitudinal axis 17 of the tubular stent 10, although the distal long portion 72' can be parallel to the proximal half of a second expansion strut 42" of chevron-shape of second expansion strut 42" pair in a second expansion column 32", or non-parallel to the longitudinal axis 17 of the tubular stent 10, as alternative configurations. A first connecting strut proximal section and a first connecting strut distal section are ipsilateral mirror images to each other, with their terminal ends 62' and 64' both pointing downward as they attach to their respective ipsilateral attachment sites on the outer top side of the apposed closed loop 48' and 48" of chevron-shaped expansion strut 42' and 42" pairs.

A first connecting strut 44' intermediate section 74' also has a generally symmetrical configuration. A first connecting strut 44' intermediate section 74' is a symmetrical upside down trapezoid configuration with slanted slopes on each side and flat horizontal bottom in the valley forming a slot or loop. A proximal end of proximal slanted slope of the upside down trapezoid intermediate section 74' is connected to a distal end of the proximal long portion 68' of a first connecting strut 44' proximal section. A distal end of distal slanted slope of the upside down trapezoid intermediate section 74' is connected to a proximal end of the distal long portion 72' of a first connecting strut 44' distal section. The upside down trapezoid valley of an M-shaped intermediate section 74' of a first connecting strut 44' in a first connecting column 34' has its position in the inter-space between the second closed loop 48' expansion strut 42' pair in a first expansion column 32' and the second closed loop 48" expansion strut 42" pair in a second expansion column 32". In other words, the central upside down trapezoidal intermediate section 74' of the M-frame connector strut 44' does not protrude out into the central area of a stent cell space 36' formed in the tubular stent 10. The inter-connecting space between the two apposed expansion strut closed loops 48", 48"' in a second 32" and a third 32"' expansion column respectively is divided into three compartments or looped spaces by the intermediate section 74" of an M-shaped first connecting strut 44" in a second connecting strut column 34". However, the position of a upside down trapezoidal intermediate section 74' of an M-shaped intermediate section of the first connecting strut 44' can have a reverse upright position (75' in FIG. 4) without modifying the configuration of a connecting strut proximal section or distal section. Protruding out of the connector inter-space between the two apposed closed-loop 48' and 48", instead of a former position in between the two apposed closed-loops 48', 48" that defines the connector inter-space. This variation of the position and orientation of the intermediate section 74' of an M-shaped first connecting strut 44' in a first connecting column 34' in a stent 10 is within the scope of present invention.

The terminal ends 62' & 64' of an M-shaped first connecting strut 44' in a first connecting strut column 34' is attached to the ipsilateral outer top sides of the two apposed closed-loop 48', 48" strut pairs in a first expansion column 32' and a second expansion column 32", respectively. A proximal short stem 66' of proximal section of a first connecting strut 44' in a first connecting column 34' is attached to the ipsilateral outer top side of a distal end of a second expansion strut 42' of a second expansion strut 42' pair of chevron shape in a first expansion column 32', and a distal short stem 70' of distal section of the first connecting strut 44' in a first connecting column 34' is attached to the ipsilateral outer top side of a proximal end of a second expansion strut 42" of a second expansion strut 42" pair of chevron shape in a second expansion column 32". Both the proximal end 62' and distal end 64' of a first connecting strut 44' in a first connecting column 34' point downward in a same direction to attach to the outer top ipsilateral sides of the two apposed closed-loop 48', 48" in a first 32' and second 32" expansion columns, respectively. Each of six (6) M-frame connecting struts 44' in a first connecting column 34' connects the first expansion column 32' to the second expansion column 32" in a manner identical to the first connecting strut 44' in the first connecting column 44' as described foregoing, in an unbroken chain-mesh pattern around the circumference 18 of the tubular stent 10. The number of connecting struts 44' in a first connecting strut column 34' can be changed to more or less number than six (6), according to the prescribed demand of a tubular stent 10 made of present invention. Variations in number of M-frame connecting struts 44' in a first connecting column 34' is within the scope of a tubular stent 10 of present invention. Likewise, skipping of the connection of an M-shaped first connecting strut between the two apposed expansion columns can be made. This skipping of interconnection with the M-shaped first connecting strut between the two companion expansion columns are within the scope of present invention.

In FIGS. 1 and 3, there are six (6) M-frame connectors 44' in a first connector column 34' coupling the first 32' and second 32" expansion columns, with all the M-frame connectors assuming upright positions. However, the position of first M-shaped connecting struts 44' in a first connecting column 34' can have a mixture of some in upright positions and some in upside down positions. By mixing upright and upside down positions of the M-shaped connecting struts 44' in a first connecting column 34" can enhance a certain flexibility and performance characteristics. A mixing pattern of three consecutive upright and three consecutive upside down positions of the M-frame connectors 44' in a first connecting column 34' could change the flexibility and trackability characteristics of a tubular stent 10 of present invention. An alternating mixture of upright and upside down positions of the M-frame connector 44' can be made in a first connecting column also. Variability of the M-frame connector 44' attachment and orientation pattern is within the scope of a tubular stent 10 of present invention. Another key feature of an M-frame connector 44 is a variable connector 44 width. In most coronary application, an M-frame connector 44 width would be narrower than a width of a closed-loop 48 expansion strut 42 pair, where an M-frame connector 44 is ipsilaterally attached. However, a width of an M-frame connector 44 could be made same or wider than a width of a closed-loop 48 expansion strut 42 pair, where an M-frame connector 44 is ipsilaterally attached.

A third expansion column 32" consists of a plurality of third expansion strut pairs of generally a chevron-shape in upright position with the apices 33''' or 43''' of the chevron pointing upward. A first expansion strut 42''' pair includes a first expansion strut 42''' of a chevron-shape with a simple-apex 43''' pointing upright, adjacent to a second expansion 42''' strut of a chevron-shape with the vertex 43''' pointing upright, which has a stepped-apex 33''' configuration at the center and is dissimilar to the first expansion strut 42''' configuration. A first joining strut 46''' couples the first and second expansion struts 42''' of chevron-shape at a proximal end of a first expansion strut 42''' pair to form a closed loop 48'''. When a first expansion strut 42''' pair is joined by a first joining strut 46''' to form a closed loop 48''', a chevron-shaped slot is formed inside the first expansion strut pair, with a narrower slot width in the closed-end half 41''' and a wider slot width in the open-end half 40''', due to the dissimilar chevron-shapes of the first and second first expansion struts 42''' of a first expansion strut pair. A second expansion strut 42''' pair includes a third expansion strut 42''' of chevron-shape with a simple-apex 43''' pointing upright, adjacent to a second expansion strut 42''' of chevron-shape with the vertex 33''' pointing upright, which has a stepped-apex configuration at the center and is dissimilar to the second expansion strut 42''' configuration. A second joining strut 46''' couples the second and third expansion struts 42''' at a distal end of the second expansion strut 42''' pair to form a closed loop 48'''. When a second expansion strut 42''' pair is joined by a second joining strut 46''' to form a closed loop 48''', a chevron-shaped slot is formed inside the second expansion strut 42''' pair, with a narrower slot width in the closed-end half 38''' and a wider slot width in the open-end half 39''', due to the dissimilar chevron-shapes of the second and third expansion struts 42''' of a second expansion strut 42''' pair. A third expansion strut 42''' pair includes a fourth expansion strut 42''' of chevron-shape with a stepped-apex 33''' pointing upright, which is dissimilar to the third expansion strut 42''' configuration, adjacent to a third expansion strut 42''' of chevron-shape with a simple apex 43''' pointing upright. A third joining strut 46''' couples the third and fourth expansion struts 42''' at a proximal end of the third expansion strut 42''' pair to form a closed loop 48'''. When a third expansion strut 42''' pair is joined by a third joining strut 46''' to form a closed loop 48''', a chevron-shaped slot is formed inside the third expansion strut 42''' pair, with a narrower slot width in the closed-end half 41''' with and a wider slot width in the open-end half 40''', due to the dissimilar chevron-shapes of the third and fourth expansion struts 42''' of a third expansion strut 42''' pair. A fourth expansion strut 42''' pair includes a fifth expansion strut of chevron-shape with a simple-apex 43''' pointing upright, adjacent to a fourth expansion strut 42''' of chevron-shape with a stepped-apex 33''' pointing upright, which is dissimilar to the fourth expansion strut 42''' configuration. A fourth joining strut 46''' couples the fourth and fifth expansion struts 42''' at a distal end of the fourth expansion strut 42''' pair. When a fourth expansion strut 42''' pair is joined by a fourth joining strut 46''' to form a closed loop, a chevron-shaped slot is formed inside the fourth expansion strut 42''' pair, with a narrower slot width in the closed-end half 38''' and a wider slot width in the open-end half 39''', due to dissimilar chevron-shapes of the fourth and fifth expansion struts 42''' of a fourth expansion strut 42''' pair. These expansion strut 42''' pairs of two dissimilar chevron-shape coupled by a joining strut 46''' to form a closed loop 48''' at an alternating proximal or distal end of the expansion strut 42''' pairs can be repeated to make the prescribed number of expansion strut 42''' pairs in an unbroken fashion around the circumference 18 in a tubular stent 10 of present invention. A set of two consecutive chevron-shaped expansion strut 42''' pairs in an unbroken sequence is called expansion strut cycles. In this application, FIGS. 1 and 3 contain six (6) chevron-shaped expansion strut 42''' pair cycles or twelve (12) chevron-shaped expansion strut 42''' pairs in a third expansion column 32''' in the 2-dimensional cut-open drawings. However, the number of chevron-shaped expansion strut 42''' pairs or expansion strut 42''' pair cycles in a third expansion column 32''' can variably be changed according to the application requirements of the specific stent 10 made of present invention. Variation of the number of expansion strut 42''' pairs or expansion strut 42''' pair cycles in a third expansion column 32''' is within the scope of a tubular stent 10 of present invention.

Although the FIGS. 1, 2 and 3 shows only a neutrally arranged upright expansion strut 42''' pairs of chevron-configuration within the first 32', second 32" or third 32''' expansion strut columns; the expansion strut 42 pairs of upright chevron-shape can be arranged in any tilted angulation within their assigned expansion columns 32', 32", 32'''. The first and second expansion struts 42''' of upright chevron-shape in a first expansion strut 42''' pair in a third expansion column 32''' are parallel to each other, but the first and second expansion struts 42''' of chevron-shape in a first expansion strut 42''' pair in a third expansion column 32''' do not parallel to the longitudinal axis of the tubular stent. The proximal or distal half of a first expansion strut pair in the second expansion column can be arranged to parallel to the longitudinal axis of the stent. Such an arrangement would also change the axis of the connecting tem of the connector strut between the two companion expansion columns. However, the first and second expansion struts 42''' of chevron-shape in a first expansion strut 42''' pair in a third expansion column 32''' do not have to parallel to each other. Both the parallel and non-parallel arrangement of the first and second expansion struts 42''' of chevron-shape in a first expansion strut 42''' pair in a third expansion column 32''' is within the scope of a tubular stent 10 of present invention. In further amplifying these strut alignment details, the expansion strut 42''' pair can be elaborated further. In a pair of chevron-shaped expansion strut 42''', the simple chevron configuration such as the first expansion strut 42''' of the first expansion strut 42''' pair in a third expansion column 32''' has two axes 60''' and 61''' divided at the center by a simple-apex 43'''; whereas a stepped-apex chevron configuration such as the second expansion strut 42''' of the first expansion strut 42''' pair in a third expansion column 32''' has two axes 58''' and 59''' divided at the center by a vertex 33'''. In FIGS. 2 and 3, the axes 58''' and 60''' parallel to each other but they 58''', 60''' do not parallel to the longitudinal axis 17 of a tubular stent 10. However, the expansion strut 42'' axes 58''' and 60''' do not have to parallel to each other. Likewise, the axes 59''' and 61 ''' of the first expansion strut 42''' pair parallel to each other but they 59''', 61''' do not parallel to the longitudinal axis 17 of a tubular stent 10. However, the expansion strut axes 59''' and 61''' do not have to parallel to each other.

The first and second expansion struts 42''' of chevron-shape in a first expansion strut 42''' pair in a third expansion column 32''' can be made of dissimilar chevron patterns as shown in FIGS. 1, 2 and 3. However, the first and second expansion struts 42''' of chevron-shape in a first expansion strut 42''' pair in a third expansion column 32''' can be made of similar chevron-shapes; the first and second expansion struts 42''' in a first expansion strut 32''' pair may consists of two simple-apex chevron-shape struts 43''' or the first and second expansion struts 42''' in a first expansion strut 42''' pair may consists of two stepped-apex chevron-shape struts 33'''. Any other variations of basic chevron configuration of similar or dissimilar combination in a first expansion strut 42''' pair in a third expansion column 32''' are within the scope of chevron-shape expansion strut 42''' configuration of a tubular stent 10 of present invention.

A first expansion strut 42''' pair first corner 54''' is formed where the first joining strut 46''' is coupled to the first expansion strut 42''' of chevron-shape, and a first expansion strut 42''' pair second corner 56''' is formed where the first joining strut 46''' is coupled to the second expansion strut 42''' of chevron-shape. A second expansion strut 42''' pair first corner 54''' is formed where the second joining strut 46''' is coupled to the second expansion strut 42''' of chevron-shape, and a second expansion strut 42''' pair second corner 56''' is formed where the second joining strut 46''' is coupled to the third expansion strut 42''' of chevron-shape. A third expansion strut 42''' pair first corner 54''' is formed where the third joining strut 46''' is coupled to the third expansion strut 42''' of chevron-shape, and a third expansion strut 42''' pair second corner 56''' is formed where the third joining strut 46''' is coupled to the fourth expansion strut 42''' of chevron-shape. A fourth expansion strut 42''' pair first corner 54''' is formed where the fourth joining strut 46''' is coupled to the fourth expansion strut 42''' of chevron-shape, and a fourth expansion strut 42''' pair second corner 56''' is formed where the fourth joining strut 46''' is coupled to the fifth expansion strut 42'''. This process of forming the first and second corner 54''', 56''' in a first expansion strut 42''' pair is repeated until all the expansion strut 42''' pairs in a third expansion column 32''' are joined with their respective joining struts 46''' to form the first 54''' and second 56''' corners for each of the closed loop 48''' expansion strut 42''' pair.

A second connecting strut column 34" is formed of a plurality of second connecting struts 44" of roughly symmetrical M-frame shape in upside down position. A first connecting strut 44" of the first connecting strut column 34" includes a connecting strut proximal section; a connecting strut distal section and a connecting strut intermediate section 74". A first connecting strut proximal section has two parts; a short stem 66" that is coupled at a perpendicular or slant angle, with its end 62", to the lower outer side of the distal end of a second expansion strut 42" of first expansion strut 42" pair in a second expansion column 32", and a proximal long portion 68" that is coupled to the proximal short stem 66" proximally and to the intermediate section 74" distally. The proximal long portion 68" generally parallels to the longitudinal axis 17 of the tubular stent 10, although the proximal long portion 68" can be parallel to the distal half of a second expansion strut 42" of chevron-shape of first expansion strut 42" pair in a second expansion column 32", or can be non-parallel to the longitudinal axis 17 of the tubular stent 10, as alternative configurations. A first connecting strut 44" distal section also has two parts; a distal short stem 70" that is coupled at a perpendicular or slant angle, with its end 64", to the lower outer side of the proximal end of a second expansion strut 42''' of first expansion strut 42''' pair in a third expansion column 32''', and a proximal long portion 72" that is coupled to the proximal short stem 70"distally and to the intermediate section 74" proximally. The distal long stem 72" generally parallels to the longitudinal axis 17 of the tubular stent 10, although the distal long portion 72" can be parallel to the proximal half of a second expansion strut 42''' of chevron-shape of first expansion strut 42''' pair in a third expansion column 32''', or can be non-parallel to the longitudinal axis 17 of the tubular stent 10, as alternative configurations. A first connecting strut 44" proximal section 66" & 68" and a first connecting strut 44" distal section 70" & 72" are ipsilateral mirror images to each other, with their terminal ends 62", 64" both pointing upward in a same direction as they attach to their respective ipsilateral attachment sites on the lower outer side of the apposed closed loop 48", 48''' chevron expansion strut 42", 42''' pairs in two adjacent second 32" and third 32''' expansion columns.

A first connecting strut 44" intermediate section 74" has a generally symmetrical configuration. A first connecting strut 44" intermediate section 74" is a symmetrical upright trapezoidal configuration with slanted slopes on each side and flat horizontal plateau at the top. A proximal end of proximal slanted slope of the upright trapezoidal intermediate section 74" is connected to a distal end of the proximal long portion 68" of a first connecting strut 44" proximal section. A distal end of distal slanted slope of the upright trapezoidal intermediate section 74" is connected to a proximal end of the distal long portion 72" of a first connecting strut 44" distal section. The upright plateau of a trapezoidal-shaped intermediate section 74" of an M-frame shaped first connecting strut 44" in a second connecting column 34" is placed in the inter-space between the first closed loop 48" expansion strut 42" pair in a second expansion column 32" and the first closed loop 48''' expansion strut 42''' pair in a third expansion column 32'''. In other words, an upright trapezoidal intermediate section 74" with horizontal plateau, of a first M-frame connector 44" does not protrude out into the central area of a stent cell space 36" formed in the tubular stent 10. The inter-connecting space between the two apposed expansion strut closed loops 48", 48" in a second 32" and a third 32''' expansion column respectively is divided into three compartments or looped spaces by the intermediate section 74" of an M-shaped first connecting strut 44" in a second connecting strut column 34". However, the position of a trapezoidal intermediate section 74" of an M-shaped first connecting strut 44" can have a reverse upside down position (75" in FIG. 4) without modifying the configuration of a first connecting strut proximal section or distal section, protruding out of the inter-space between the two apposed closed-loop 48", 48''' expansion strut 42", 42''' pairs, out into the central cell space 36". Variations of position and orientation of the trapezoidal intermediate section 74" of an M-shaped first connecting strut 44" in a second connecting column 34" is within the scope of M-shaped connecting strut 44" of the stent 10 of present invention.

The terminal ends 62", 64" of an M-shaped first connecting strut 44" in a second connecting strut column 34" is attached to the lower ipsilateral outer sides of the two apposed closed-loop 48", 48''' expansion strut 42", 42''' pairs in a second 32" and a third 32''' expansion columns, respectively. A proximal short stem 66" of proximal section of a first connecting strut 44" in a second connecting column 34" is attached to the lower ipsilateral outer side of a distal end of a second expansion strut 42" of a first expansion strut 42" pair of chevron shape in a second expansion column 32", and a distal short stem 70" of distal section of the first connecting strut 44" in a second connecting column 34" is attached to the lower ipsilateral outer side of a proximal end of a second expansion strut 42''' of a first expansion strut 42''' pair of chevron shape in a third expansion column 32'''. Both the proximal end 62" and distal end 64" of an M-frame first connecting strut 44" in a second connecting column 34" point upward in a same direction to attach to the lower outer ipsilateral sides of the two apposed closed-loop 48", 48''' expansion strut 42", 42''' pairs of the second 32" and third 32''' expansion columns, respectively. Each of six (6) M-frame connecting struts 44" in a second connecting column 34" connects the second expansion column 32" to the third expansion column 32''' in a manner identical to the first connecting strut 44" in a second connecting column 34", as described in the foregoing paragraphs, in an unbroken chain-mesh pattern around the circumference 18 of the tubular stent 10. The number of connecting struts 44" in a second connecting strut column 34" can be changed to more or less number than six (6) connecting struts 44", according to the prescribed demand of a tubular stent 10 made of present invention. Variations in number of M-frame connecting struts 44" in a second connecting column 34" is within the scope of a tubular stent 10 of present invention. Likewise, skipping of the connection of an M-shaped first connecting strut between the two apposed expansion columns can be made. This skipping of interconnection with the M-shaped first connecting strut between the two companion expansion columns are within the scope of present invention.

In FIGS. 1, 2 & 3, there are six (6) M-frame connectors 44" in a second connector column 34" coupling the second 32" and third 32''' expansion columns, with all the M-frame connectors 44" assuming upside down positions. However, the position of second M-shaped connecting struts 44" in a second connecting column 34" can have a mixture of some in upright position and some in upside down position. By mixing upright and upside down positions of the M-shaped connecting struts 44" in a second connecting column 34" can enhance a certain flexibility and performance characteristics of the stent 10 made of present invention. An alternating mixture of upright and upside down positions of the M-frame connector 44' can be made in a first connecting column also. A mixing pattern of three consecutive upright and three consecutive upside down positions of the M-frame connectors 44" in a second connecting column 34" could change the flexibility and trackability characteristics of a tubular stent 10 of present invention. Variability of the M-frame connector 44" attachment orientation and pattern is within the scope of a tubular stent 10 of present invention.

Another key feature of an M-frame connector 44" is a variable connector width. In most coronary application, an M-frame connector strut 44 width would be narrower than a width of a closed-loop 48 expansion strut 42 pair, where an M-frame connector strut 44 is ipsilaterally attached. However, a width of an M-frame connector strut 44 could be made same or wider than a width of a closed-loop 48 expansion strut 42 pair, where an M-frame connector strut 44 is ipsilaterally attached.

Figure 4:
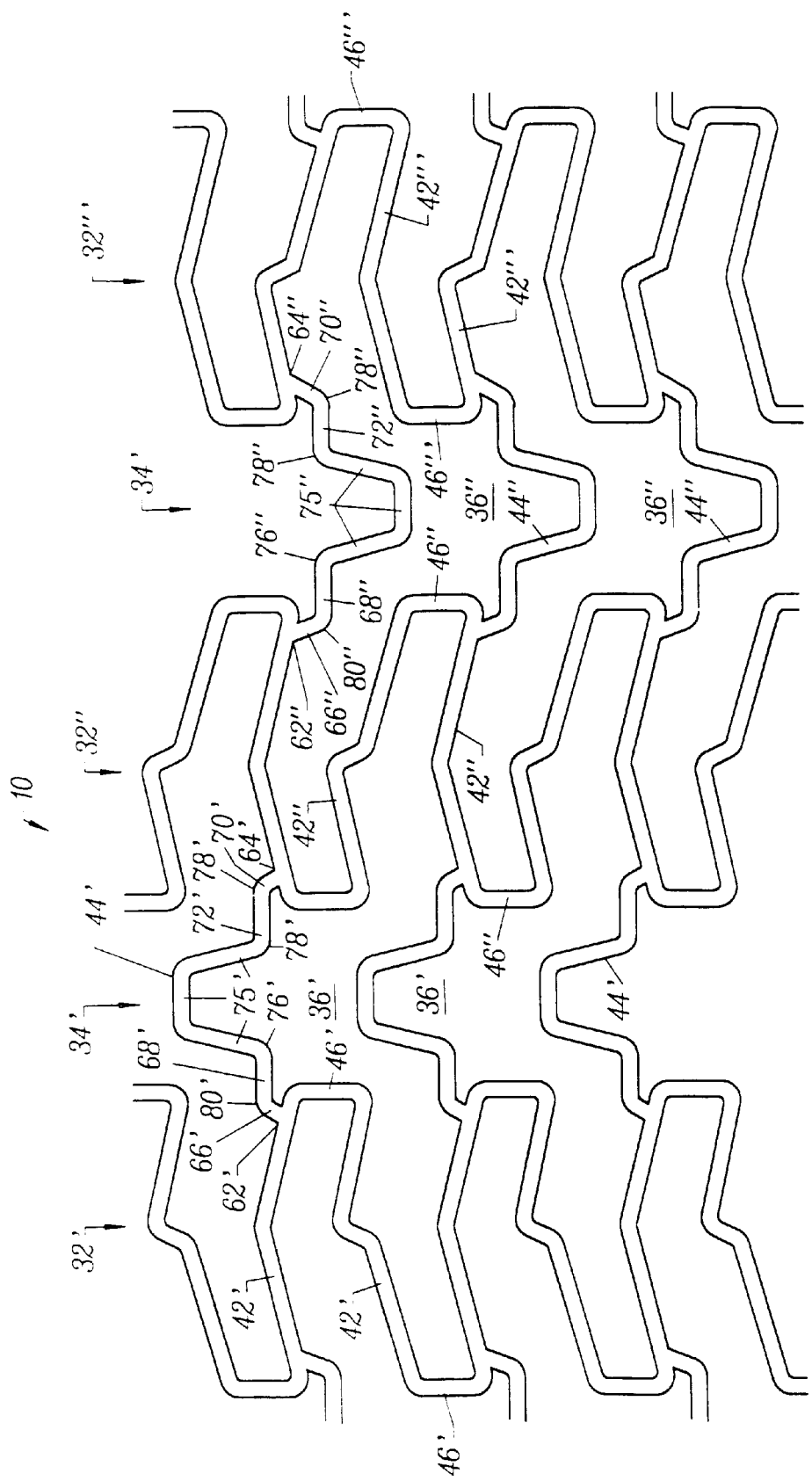
FIG. 4—An alternative configuration of the intermediate section of the connector in addition to the connector configuration described in FIG. 1–3.

FIG. 4—This figure is used to illustrate an alternative configuration and orientation of the intermediate section 75' of a first connecting strut 44' in a first connecting column 34' in comparison to the configuration and orientation of the intermediate section 75' of a first connecting column 34'. In these schematic drawings of FIG. 2 and 4, although the configuration and orientation of the intermediate section 75' of a first and second connecting strut 44' in the first and second connecting columns 34', 34" in FIG. 4 are different from the configuration and orientation of the intermediate section 74 of a first and second connecting strut 44 in the first and second connecting column 34 in FIG. 2, the configuration and orientation of the closed loop 48 expansion strut 42 pairs in the expansion columns 32 in FIG. 4 are exactly same as in FIG. 2. Whereas in FIG. 2, the intermediate section 74' of the first connecting strut 44' in a first connecting column 34' is invaginated, or inward-oriented, into the inter-space between the second closed loop 48' expansion strut 24' pair in a first expansion column 32' and the second closed loop 48" expansion strut 42" pair in a second expansion column 32", the intermediate section 75' of a first connecting strut 44' in a first connecting column 34' in FIG. 4 is evaginated, or outward-oriented, into the central cell space 36'. The trapezoid geometry of the intermediate section 74' of FIG. 2 is identical to the trapezoid geometry of the intermediate section 75' of FIG. 4, except for the fact that the horizontally flat valley bottom of the intermediate section 74' of a first connecting strut 44' in a first connecting strut column 34' is invaginated, or inward-oriented, in FIG. 2 and the horizontal plateau top of the intermediate section 75' of a first connecting strut 44' in a first connecting strut column 34' is evaginated, or outward-oriented, in FIG. 4. The proximal short stem 66' and proximal long portion 68' of a first connecting strut 44' of FIG. 2 and the proximal short stem 66' and proximal long portion 68' of a first connecting strut 44' of FIG. 4 are identical and unchanged, despite the fact that the configuration and orientation of intermediate sections 74' and 75' are dissimilar in the respective figures. Likewise, the distal long portion 72' and distal short stem 70' of a first connecting strut 44' in FIG. 2 and the distal long portion 72' and distal short stem 68' of a first connecting strut 44' in FIG. 4 are also identical and unchanged, despite the fact that the configuration and orientation of intermediate sections 74' and 75' in their respective figures are dissimilar. The proximal terminal end 62' and the distal terminal end 64' of a first connecting strut 44' in a first connecting column 34' of FIG. 2 point down ward in a same direction as they couple to their ipsilateral attachment sites, exactly same as the proximal terminal end 62' and the distal terminal end 64' of a first connecting strut 44' in a first connecting column 34' of FIG. 4 point down ward in a same direction as they couple to their ipsilateral attachment sites. The configuration of a proximal short stem 66" and proximal long portion 68" of a second connecting strut 44" in a second connecting column 34" in FIG. 4 is exactly same as the configuration of the proximal short stem 66" and proximal long portion 68" of a second connecting strut 44" in a second connecting column 34" of FIG. 2. Likewise, the configuration of the distal short stem 70' and proximal long portion 72' of a second connecting strut 44" in a second connecting column 34" of FIG. 4 is exactly same as the configuration of the distal short stem 70' and distal long portion 72' of a second connecting strut 44" in a second connecting column 34" of FIG. 2.

The second connecting strut 44" in a second connecting column 34" are identical in their geometric configuration or shape to the first connecting strut 44' in a first connecting column 34', although they are oriented in 180 degree opposite directions. Whereas the terminal ends 62' and 64' of a first connecting strut 44' in a first connecting column 34' are pointed downward in one direction as they couple to their ipsilateral attachment sites, the terminal ends 62" and 64" of a second connecting strut 44" in a second connecting column 34" are pointed upright in a different direction as they couple to their ipsilateral attachment sites.

Figure 5:
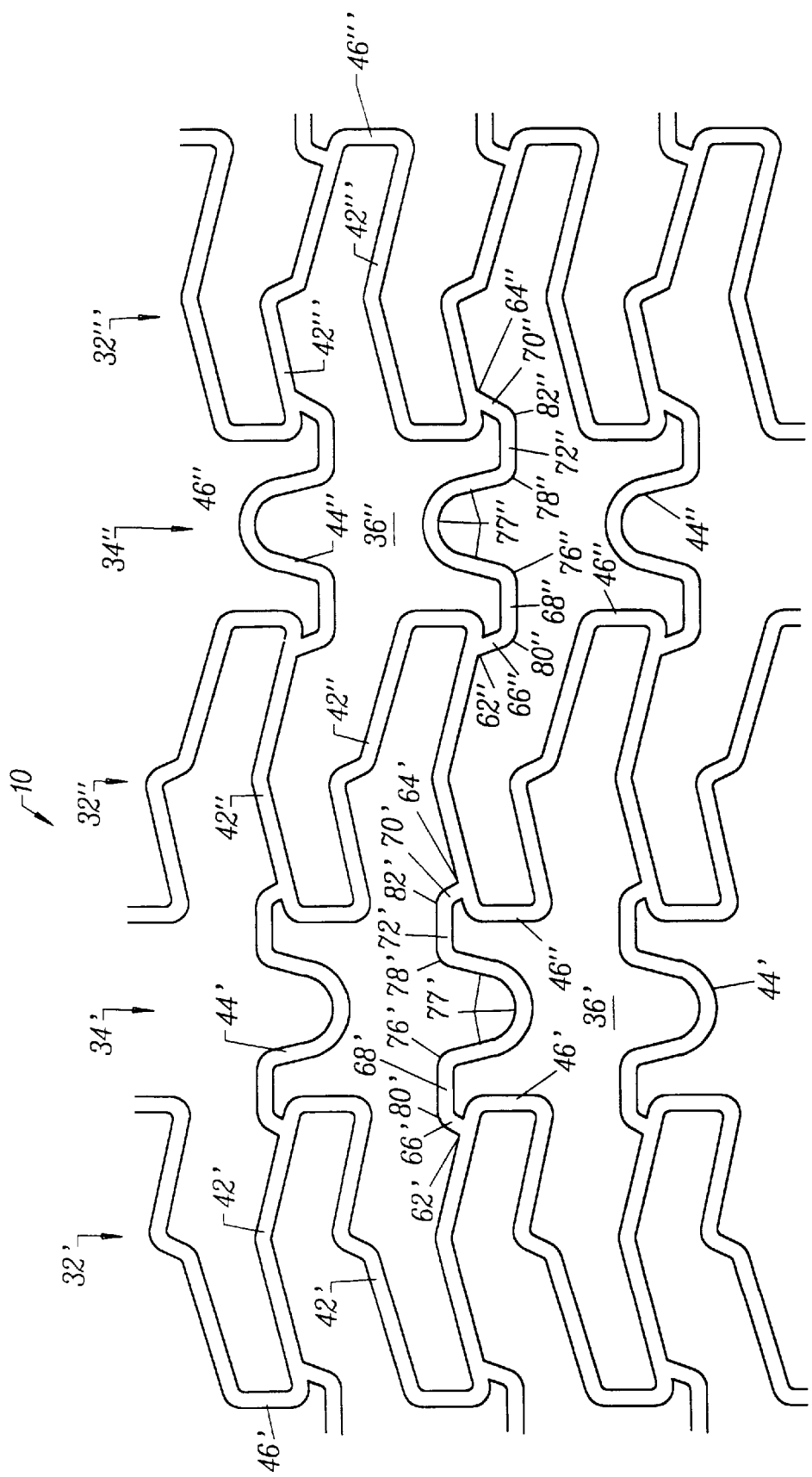
FIG. 5—Yet another alternative configuration of the connector strut in addition to the connector configurations described in FIG. 1–4.

FIG. 5—This schematic drawing illustrates yet another variation of the configuration of the connecting struts 44 in the connecting columns 34. This figure will be compared to FIG. 2 to describe the configuration difference of the intermediate section 77 of the connecting strut 44 of FIG. 5. The configuration of the intermediate sections 77' and 77" of a first and second connecting struts 44' and 44" in the first and second connecting columns 34' and 44" respectively in FIG. 5 are different from the configuration of the intermediate sections 74' and 74" of a first and second connecting strut 44' and 44" in the first and second connecting column 34' and 34" respectively in FIG. 2 & 3. Whereas the configuration of the intermediate section 74' and 74" of the connecting struts 44' and 44" respectively have trapezoidal shape with horizontal valley bottom or flat plateau top in FIG. 2 & 3, the intermediate section 77' and 77" of the connecting struts 44' and 44" respectively have curvilinear or semicircular shape in FIG. 5. The configuration and orientation of the closed loop 48', 48", 48''' expansion strut 42', 42", 42''' pairs in the expansion columns 32', 32" and 32''' respectively in FIG. 5 are exactly same as in FIGS. 2 & 3. In FIGS. 2 & 3, the intermediate sections 74' of the first connecting struts 44' in a first connecting columns 34' has invagination, or inward-protrusion, into the inter-space between the closed loops 48' in a first expansion column 32' and the closed loops 48" in a second expansion column 32". Likewise, in FIG. 5 the intermediate sections 77' a first connecting struts 44' in the first connecting columns 34' also has invagination, or inward-protrusion, into the inter-space between the first closed loops 48' in a first expansion column 32' and the second closed loops 48" in a second expansion column 32". Like the trapezoidal shape intermediate section 74' in FIGS. 2 & 3, the curvilinear shape intermediate section 77" in FIG. 5 divides the inter-connecting space between the two connecting points into three (3) compartments or looped spaces. In FIGS. 2 & 3, the intermediate sections 74" of the second connecting struts 44" in a second connecting columns 34" also has invagination, or inward-protrusion, into the inter-space between the closed loops 48" in a second expansion column 32" and the closed loops 48''' in a third expansion column 32'''. In FIG. 5, the intermediate sections 77" of a second connecting struts 44' in the second connecting columns 34" also has invagination, or inward-protrusion, into the inter-space between the closed loops 48" in a second expansion column 32" and the closed loops 48''' in a third expansion column 32'''. Like the trapezoidal shape intermediate section 74" in FIGS. 2 & 3, the curvilinear shape intermediate section 77" in FIG. 5 divides the inter-connecting space between the two connecting points into three (3) compartments or looped spaces.

The curvilinear geometry of the intermediate section 77' and 77" of the connector struts 44' and 44" in FIG. 5 are identical, except for the fact that the curvilinear dome-shaped top of the intermediate section 77' and the curvilinear dome-shaped bottom of intermediate section 77" are oriented in 180 degree opposite directions. Whereas the terminal ends 62' and 64' of a first connecting strut 44' in a first connecting column 34' are pointed downward in one direction as they couple to their ipsilateral attachment sites, the terminal ends 62" and 64" of a second connecting strut 44" in a second connecting column 34" are pointed upright in another direction as they couple to their ipsilateral attachment sites.

Figure 6:
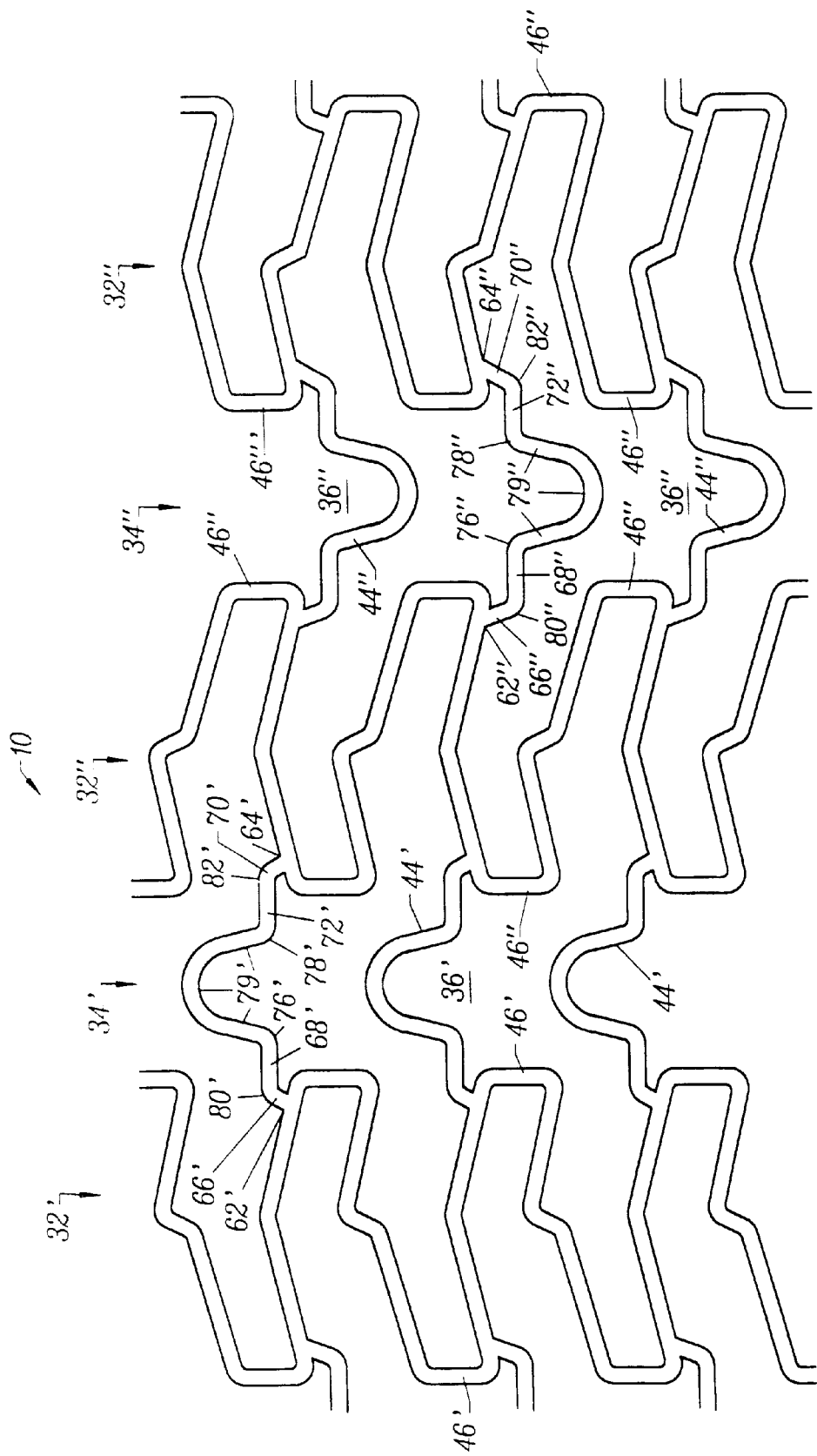
FIG. 6—A variation of the connector configuration different from the connector configurations described in FIG. 1–5.

FIG. 6—This FIG. 6 is a counterpart to FIG. 4 in that the curvilinear shape intermediate section 79 of a connecting strut 44 has evagination, or outward orientation, into the central cell space 36 like the trapezoidal shape intermediate section 75 of connecting strut 44 in FIG. 4, although the curvilinear shape of the intermediate section 79 in FIG. 6 is dissimilar to the trapezoidal shape of the intermediate section 75 in FIG. 4. The shape of an intermediate section 79 of a connecting strut 44 in a connecting column 34 in FIG. 6 is different from the shape of the intermediate section 75 of a connecting strut 44 in a connecting column 34 in FIG. 4.

What is claimed is:

1. A stent in a non-expanded state, comprising:
   a first expansion column including a plurality of expansion strut pairs, a first expansion strut pair in the first column including a first expansion strut, a second expansion strut and a joining strut, the first expansion strut pair forming a chevron shaped slot in the first expansion column, the expansion struts in the first expansion strut column each having a chevron shape, and one of the expansion struts in the first expansion strut column having a stepped apex;
   a second expansion column including a plurality of expansion strut pairs, a first expansion strut pair in the second expansion column including a first expansion strut, a second expansion strut and a joining strut, a first expansion strut pair in the second expansion column forming a chevron shaped slot in the second expansion column, at least one of the expansion struts in the second expansion column having a chevron shape; and
   plurality of first serial connecting struts forming a first serial connecting strut column, the plurality of first serial connecting struts coupling the first expansion column to the second expansion column, a first serial connecting strut in the first serial connecting strut column coupling the second expansion strut of the first expansion column to the second expansion strut of the second expansion column.

2. The stent of claim 1, wherein the first serial connecting strut of the first serial connecting strut column has an "M"-shaped geometric configuration.

3. The stent of claim 1, wherein the first serial connecting strut of the first serial connecting strut column has a trapezoidal geometry loop configuration in a middle of the first serial connecting strut.

4. The stent of claim 1, wherein the first serial connecting strut of the first serial connecting strut column defines a first serial connecting strut first, second and third loops in a connecting space between the first and second expansion column.

5. The stent of claim 4, wherein the first serial connecting strut of the first serial connecting strut column divides the connecting space into three compartments.

6. The stent of claim 4, wherein the first and third loops in the connecting space extend in a first direction and the second loop extends in a second direction.

7. The stent of claim 3, wherein a trapezoidal geometry intermediate section of the first serial connecting strut in the first serial connecting strut column has a 180° direction change, moving out of the connecting space and protruding into a center of a stent cell space.

8. The stent of claim 3, wherein an intermediate section of the first serial connecting strut in the first serial connecting strut column has a curvilinear geometry loop configuration that divides a connecting space into three compartments.

9. The stent of claim 3, wherein a trapezoid geometry intermediate section of the first serial connecting strut in the first serial connecting strut column has a curvilinear geometry loop configuration that protrudes into a center of a stent cell space.

10. The stent of claim 1, wherein the first expansion strut pair in the first column land the second expansion strut pair in the second column each define a quasi-chevron shaped slot.

11. The stent of claim 1, wherein the first and second expansion struts of the first and second expansion columns each have a first section and a second section.

12. The stent of claim 11, wherein the first and second sections of the first expansion strut of the first expansion strut pair in the first expansion strut column are coupled to form a stepped apex section, and the first and second sections of the first expansion strut of the first expansion strut pair in the second expansion column are coupled to form a stepped apex section.

13. The stent of claim 12, wherein the first and second sections of the second expansion strut of the first expansion strut pair in the first expansion strut column are coupled to form a simple apex, and the first and second sections of the second expansion strut of the first expansion strut pair in the second expansion column are coupled to form a simple apex.

14. The stent of claim 13, wherein the apeces of the first expansion column all extend in a same direction.

15. The stent of claim 13, wherein the apeces of the second expansion column all extend in a same direction.

16. The stent of claim 13, wherein the first section of the first expansion strut of the first expansion strut pair in the first expansion column and the first section of the second expansion strut of the first expansion strut pair in the first expansion column are separated by a first length, and the second section of the first expansion strut of the first expansion strut pair in the first expansion column and the second section of the second expansion strut of the first expansion strut pair in the first expansion column are separated by a second length, wherein the second length is greater than the first length.

17. The stent of claim 16, wherein the first section of the first expansion strut of the first expansion strut pair in the first expansion column has a longitudinal axis that is parallel to a longitudinal axis of the first section of the first expansion strut of the first expansion strut pair in the second expansion column.

18. The stent of claim 17, wherein the second section of the first expansion strut of the first expansion strut pair in the first expansion column has a longitudinal axis that is parallel to a longitudinal axis of the second section of the first expansion strut of the first expansion strut pair in the second expansion column.

19. The stent of claim 18, wherein the first sections of the first and second expansion strut of the first and second expansion columns are parallel to each other, and the second sections of the first and second expansion struts of the first and second expansion columns are parallel to each other.

20. The stent of claim 11, wherein each of a first and second section of a first and second expansion struts in the first and second expansion columns has a longitudinal axis that is non-parallel to a longitudinal axis of the stent.

21. The stent of claim 1, wherein each of the first serial connecting struts of the first serial connecting strut column has a proximal portion with a proximal stem, a distal portion with a distal stem and an intermediate portion that couples the proximal and distal portions.

22. The stent of claim 21, wherein the proximal stem of the first serial connecting strut is ipsilaterally coupled to a first side of the second section of the second expansion strut of the first expansion strut pair in the first expansion column, and the distal stem is ipsilaterally coupled to a first side of the first section of the second expansion strut of the first expansion strut pair in the second expansion column.

23. The stent of claim 22, wherein the proximal and distal stems of the first serial connecting strut each extend in a same direction.

24. The stent of claim 22, wherein the proximal stem of the first serial connecting strut is coupled to the side of the second section of the second expansion strut at a connect angle of 85° or greater, wherein the connect angle is formed closest to the simple apex.

25. The stent of claim 22, wherein the proximal stem of the first serial connecting strut is coupled to the side of the second section of the second expansion strut at a connect angle of about 90° or greater, wherein the connect angle is formed closest to the simple apex.

26. The stent of claim 22, wherein the distal stem of the first serial connecting strut is coupled to the side of the first section of the second expansion strut at a connect angle of 85° or greater, wherein the connect angle is formed closest to the simple apex.

27. The stent of claim 22, wherein the distal stem of the first serial connecting strut is coupled to the side of the first section of the second expansion strut at a connect angle of about 90° or greater, wherein the connect angle is formed closest to the simple apex.

28. The stent of claim 1, wherein the first and second expansion columns are each unbroken, continuous tubular structures.

29. A stent in a non-expanded state, comprising:
a first column expansion strut pair including a first expansion strut, a second expansion strut and a joining strut, a plurality of the first column expansion strut pairs forming a first expansion column, the expansion struts in the first expansion column each having a chevron shape, and one of the expansion struts in the first expansion column having a stepped apex;
a second column expansion strut pair including a first expansion strut, a second expansion strut and a joining strut, a plurality of the second column expansion strut pairs forming a second expansion column, the expansion struts in the second expansion column each having a chevron shape, and one of the expansion struts in the second expansion column having a stepped apex; and
a first serial connecting strut, a plurality of first serial connecting struts forming a first serial connecting strut column, the plurality of first serial connecting struts coupling the first expansion column to the second expansion column, the first serial connecting strut ipsilaterally coupling the second expansion strut of the first expansion column to the second expansion strut of the second column;

a third column expansion strut pair including a first expansion strut, a second expansion strut and joining strut, a plurality of the third column expansion strut pairs forming a third expansion column, the expansion struts in the third expansion column each having a chevron shape, and one of the expansion struts in the third expansion column having a stepped apex; and a first serial connecting strut, a plurality of first serial connecting struts forming a second serial connecting strut column, the plurality of first serial connecting struts coupling the second expansion column to the third expansion column, the first serial connecting strut ipsilaterally coupling the second expansion strut of the second expansion column to the second expansion strut of the third expansion column.

30. The stent of claim 29, wherein the first serial connecting strut of the second serial connecting strut column has an "M"-shaped geometric configuration.

31. The stent of claim 29, wherein the first serial connecting strut of the second serial connecting strut column has a trapezoidal geometry loop configuration in a middle of the first serial connecting strut.

32. The stent of claim 29, wherein the first serial connecting strut of the second serial connecting strut column defines a first serial connecting strut first, second and third loops in a connecting space between the first and second expansion column.

33. The stent of claim 29, wherein the first serial connecting strut of the second serial connecting strut column divides the connecting space into three compartments.

34. The stent of claim 29, wherein the first and third loops in the connecting space extend in a first direction and the second loop extends in a second direction.

35. The stent of claim 29, wherein the first, second and third expansion column strut pairs each define a quasi-chevron shaped slot.

36. The stent of claim 29, wherein the first and second expansion struts of the second and third expansion columns each have a first section and a second section.

37. The stent of claim 36, wherein the first and second sections of the first expansion strut of the second expansion column strut pair are coupled to form a stepped apex section, and the first and second sections of the first expansion strut of the third expansion column strut pair are coupled to form a simple apex section.

38. The stent of claim 37, wherein the first and second sections of the second expansion strut of the second expansion column strut pair are coupled to form a simple apex, and the first and second sections of the second expansion strut of the third expansion column strut pair are coupled to form a stepped apex section.

39. The stent of claim 38, wherein the apeces of the second expansion column all extend in a same direction.

40. The stent of claim 38, wherein the apeces of the third expansion column all extend in a same direction.

41. The stent of claim 38, wherein the first sections of the first and second expansion struts of the third expansion column strut pair are separated by a first length, and the second sections of the first and second expansion struts of the third expansion column strut pair are separated by a second length, wherein the second length is greater than the first length.

42. The stent of claim 41, wherein the first section of the first expansion strut of the second expansion column strut pair has a longitudinal axis that is parallel to a longitudinal axis of the first section of the first expansion strut of the third expansion column strut pair.

43. The stent of claim 42, wherein the second section of the first expansion strut of the second expansion column strut pair has a longitudinal axis that is parallel to a longitudinal axis of the second section of the first expansion strut of the third expansion column strut pair.

44. The stent of claim 36, wherein each of a first and second section of a first and second expansion struts in the second and third expansion columns has a longitudinal axis that is non-parallel to a longitudinal axis of the stent.

45. The stent of claim 29, wherein each of the first serial connecting struts of the second serial connecting strut column has a proximal portion with a proximal stem, a distal portion with a distal stem and an intermediate portion that couples the proximal and distal portions.

46. The stent of claim 44, wherein in the second serial connecting strut column, the proximal stem of the first serial connecting strut is ipsilaterally coupled to a second side of the second section of the second expansion strut of the second expansion column, and the distal stem is ipsilaterally coupled to a second side of the first section of the second expansion strut of the third expansion column.

47. The stent of claim 46, wherein the proximal and distal stems of the first serial connecting strut of the second serial connecting strut column each extend in a same direction.

48. The stent of claim 46, wherein in the second serial connecting strut column, the proximal stem of the first serial connecting strut is coupled to the side of the second section of the second expansion strut at a connect angle of 85° or greater, wherein the connect angle is formed closest to the simple apex.

49. The stent of claim 46, wherein in the second serial connecting strut column, the proximal stem of the first serial connecting strut is coupled to the side of the second section of the second expansion strut at a connect angle of about 90° or greater, wherein the connect angle is formed closest to the simple apex.

50. The stent of claim 46, wherein in the second serial connecting strut column, the distal stem of the first serial connecting strut is coupled to the side of the first section of the second expansion strut at a connect angle of 85° or greater, wherein the connect angle is formed closest to the stepped apex section.

51. The stent of claim 46, wherein the distal stem of the first serial connecting strut is coupled to the side of the first section of the second expansion strut at a connect angle of about 90° or greater, wherein the connect angle is formed closest to the stepped apex section.

52. The stent of claim 29, wherein the first, second and third expansion columns are each unbroken, continuous tubular structures.

* * * * *